(12) United States Patent
Gulati

(10) Patent No.: US 7,976,835 B2
(45) Date of Patent: Jul. 12, 2011

(54) METHODS AND COMPOSITIONS FOR PREVENTING AND TREATING SOLID TUMORS

(75) Inventor: Anil Gulati, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 445 days.

(21) Appl. No.: 11/460,202

(22) Filed: Jul. 26, 2006

(65) Prior Publication Data

US 2006/0257362 A1  Nov. 16, 2006

Related U.S. Application Data

(63) Continuation of application No. 10/691,915, filed on Oct. 23, 2003, now abandoned.

(60) Provisional application No. 60/420,960, filed on Oct. 24, 2002.

(51) Int. Cl.
*A61K 33/24* (2006.01)
*A61K 38/10* (2006.01)
*A61K 38/20* (2006.01)
*A61K 38/21* (2006.01)
*A61K 38/24* (2006.01)

(52) U.S. Cl. ............ 424/85.2; 424/85.5; 424/85.6; 424/85.7; 424/649; 514/16.1

(58) Field of Classification Search .......... 514/12, 514/267

See application file for complete search history.

(56) References Cited

U.S. PATENT DOCUMENTS

| 5,550,110 | A | 8/1996 | Cody et al. | |
|---|---|---|---|---|
| 5,612,359 | A | 3/1997 | Murugesan | |
| 5,811,416 | A | 9/1998 | Chwalisz et al. | |
| 2002/0082285 | A1 | 6/2002 | Lebwohl | |
| 2003/0104976 | A1* | 6/2003 | Davar et al. | 514/1 |

FOREIGN PATENT DOCUMENTS

| EP | 0 655 463 | 5/1995 |
|---|---|---|
| EP | 0-815 870 | 1/1998 |
| EP | 0 950 418 | 10/1999 |
| WO | WO 96/19233 | 6/1996 |
| WO | WO 00/67024 | 11/2000 |
| WO | WO 01/00198 | 1/2001 |
| WO | WO 0100198 A2 * | 1/2001 |
| WO | WO 01/91736 | 12/2001 |
| WO | WO 03/009805 | 2/2003 |
| WO | WO 03/045434 | 6/2003 |

OTHER PUBLICATIONS

Taxol® product Label (Feb. 10, 2000).*
Bell et al. (International Journal of Cancer 1999; 80: 295-302).*
Wu-Wong et al (The Journal of Pharmacology and Experimental therapeutics, 2000, vol. 293, pp. 514-521).*
Murata et al (British Journal of Pharmacology, Apr. 2001, vol. 132, pp. 1365-1373).*
Rowinsky et al. (N. Engl. J. Med. 1995; 332: 1004-1014).*
D.J. Chaplin et al., *Seminars in Radiation Oncology*, vol. 8, No. 3, pp. 151-163 (1998).
K.M. Bell et al., *Br. J. Cancer* Supp. 27:S161-3 (1996).
K.M. Bell et al., *Int. J. Cancer*, 67(5):730-8 (1996).
K.M. Bell et el., *Int. J. Cancer*, 73(2):283-9 (1997).
K.M. Bell et al., *Int. J. Cancer*, 80(2):295-302 (1999).
K. Kikuchi et al., *Biochemical and Biophysical Research Communications*, vol. 219, No. 3, 734-739 (1996).
A. Rai et al., *Cancer Chemother. Pharmacol.*, vol. 51, 21-28 (2002).
R. Lahav et al., *Proceedings of the National Academy of Sciences of USA*, vol. 96, 11496-11500 (1999).
K.M. Bell et al., *Journal of Cardiovascular Pharmacology*, vol. 26, No. s3, s222-s225 (1995).
D. DelBufalo et al., *Clinical Science*, vol. 103, No. S48, 302S-305S (2002).
J.M. Kroodsma et al., *Nederlands Tijdschrift Voor Geneeskunde*, vol. 141, No. 38, 1-3 (1997).
B. Battistini et al., *Drug News & Perspectives*, vol. 8, No. 6, 365-391 (1995).
A.P. Davenport et al., *Clinical Science*, vol. 103, No. S48, 1S-3S (2002).
K. Matsumaru et al., *J. Gastroenterol*, 32, 164-170 (1997).
A.E. Duggan et al., *Aliment Pharmacol Ther*, 13, 631-635 (1999).
A.S.C. Fabricio et al., *British Journal of Pharmacology*, 125, 542-548 (1998).
K. Parfitt (ed)., "Martindale The complete drug reference (32nd Edition)," Pharmaceutical Press, 1999.
S. Bhalla et al., *Peptides*, 23, 1837-1845 (2002).
H.N. Bhargava et al., *The Journal of Pharmacology and Experimental Therapeutics*, vol. 252, No. 3, 901-907 (1990).
C. Wu, *Exp. Opin. Ther. Patents*, 10(11), 1653-1668 (2000).
M.F. Jarvis et al., *European Journal of Pharmacology*, 388, 29-35 (2000).
G. Davar et al., *NeuroReport*, 9, 2279-2283 (1998).
Davenport, International Union of Pharmacology. XXIX. Update on Endothelin Receptor Nomenclature, 2002, vol. 54, No. 2, pp. 219-226, Journal, Pharmacological Reviews, The American Society for Pharmacology and Experimental Therapeutics.

* cited by examiner

*Primary Examiner* — Karen Canella
(74) *Attorney, Agent, or Firm* — K&L Gates LLP; Louis C. Cullman; Dean G. Stathakis

(57) ABSTRACT

Compositions and methods of preventing or treating a breast cancer are disclosed. The composition and method can utilize an endothelin B agonist and a chemotherapeutic agent as active ingredients to treat a solid tumor in mammals, including humans. Alternatively, the composition and method can utilize an endothelin B antagonist and an optional angiogenesis inhibitor to treat a solid tumor in mammals, including humans.

14 Claims, 5 Drawing Sheets

METHODS AND COMPOSITIONS FOR PREVENTING AND TREATING SOLID TUMORS

CROSS REFERENCE TO RELATED APPLICATIONS

This application is a continuation of U.S. patent application Ser. No. 10/691,915 filed on Oct. 23, 2003, which claims the benefit of U.S. provisional patent application No. 60/420,960, filed Oct. 24, 2002, the entire disclosure of which is incorporated herein by reference.

FIELD OF THE INVENTION

The present invention relates to the prevention and treatment of solid tumors, such as breast tumors, in a mammal, either by administration of therapeutically effective amounts of an endothelin agonist and a chemotherapeutic drug, or by administration of a therapeutically effective amount of an endothelin antagonist.

BACKGROUND OF THE INVENTION

Although the present specification is directed primarily to breast tumors, the invention disclosed and claimed herein can be used in the treatment and prevention of solid tumors in general, as set forth hereafter.

Breast cancer incidence has increased substantially in the last 10 years, and is the single leading cause of death for women ages 40-49 years in the United States. In 2001, 192,000 cases and 40,000 deaths made breast cancer the most common cancer, after superficial skin cancers, and the second leading cause of cancer death (Lacey et al., *Environ Mol Mutagen,* 39(2-3):82-88 (2002)).

The development of a breast cancer is a complex process involving a combination of factors, such as environmental and genetic factors. One extensively studied breast tumor model is the chemically induced rat mammary carcinogenesis model (Refs. 9, 18, 19, 39, 54). Chemically induced mammary tumorigenesis in rats is the model most closely resembling a human cancer (40).

Chemically induced rat mammary carcinogenesis typically is achieved by administration of 7,12-dimethylbenzene (a)anthracene (DMBA) (37) or N-methylnitrosourea (MNU) (37). Tumors induced by DMBA or MNU have different morphological characteristics. In particular, tumors induced by MNU are more localized at the breast and are less likely to metastasize (25). Therefore, MNU often is chosen as the chemical agent for the specific induction of breast tumors in rats. These breast tumors can be benign with fibroadenomas and papillomas, or they can be malignant (54). Rats have six pairs of mammary glands, one in the cervical region, two in the thoracic region, one in the abdominal region, and two in the ingual region (4, 54). Virgin rats treated with MNU develop more tumors in the thoracic region than the abdominal region (41).

The development of tumor vasculature has been studied extensively. Tumors greater than a few millimeters in size require a constant nutrient supply, and, therefore, have their own vascular bed and blood flow (10). Recruitment of new vasculature from preexisting blood vessels is termed "angiogenesis." Without constant nourishment from these developing blood vessels, the tumors become hypoxic and subsequently die. Therefore, tumor vasculature has been a target of cancer therapy for a considerable time (10).

Tumor blood vessels develop substantially differently from normal vasculature, and have different properties. Single layered epithelial cells are the first hastily formed tumor blood vessels. It has been suggested that these blood vessels are recruited when the tumor secretes certain growth factors, like vascular endothelial growth factor (VEGF), in response to hypoxic conditions (23). These newly formed tumor blood vessels do not have a smooth muscle layer or innervation (29, 36, 57).

Tumors also incorporate mature blood vessels that possess all their autoregulatory functions (29). Normal tissue vascular tone is governed by a host of endogenous factors like $H^+$, $K^+$, $Ca^{2+}$, $pO_2$, $pCO_2$, nitric oxide (NO), as well as other regulatory substances like endothelin (ET-1) (24, 46).

ET-1 is a potent vasoconstrictor and contributes significantly in regulating vascular tone (61). In breast cancer tissue, $ET_B$ receptors are found on stromal fibroblast cells (5, 34). Endothelins have been found to be mitogenic to fibroblasts (53), melanocytes, vascular smooth muscle, and endothelium (3, 35, 52). Investigators have shown an increase in ET-1, ET-3, and $ET_B$ receptor expression in breast carcinomas (1). It has been shown that both ET-1 and ET-3 cause an increase in VEGF, which is an important angiogenic factor (35). Thus, an increase in ET-1 promotes tumor growth. Several studies have reported an increase in ET-1 levels in breast tumors (1, 21, 31, 33, 59, 60).

The present invention is directed to the effect of endothelin antagonists and endothelin agonists on systemic hemodynamics and blood circulation in solid tumor tissues. The present invention also is directed to the use of endothelin agonists and endothelin antagonists in the treatment of solid tumors.

SUMMARY OF THE INVENTION

The present invention is directed to administration of therapeutically effective amounts of an endothelin agonist and a chemotherapeutic agent to an individual in need thereof in the treatment of a solid tumor. The present invention also is directed to administration of a therapeutically effective amount of an endothelin antagonist to an individual in need thereof in the prevention and treatment of a solid tumor, such as a breast tumor.

In particular, tumors need a blood supply to grow. ET is a powerful regulator of blood flow. $ET_A$ receptors have been found to be vasoconstrictors, and $ET_B$ receptors have been found to be vasodilators. In accordance with the present invention, it has been demonstrated that breast tumor tissue has abundant $ET_B$ receptors, and that an $ET_B$ receptor antagonist can block the increased blood flow to breast tumor tissue induced by ET-1. Accordingly, an endothelin antagonist, particularly an $ET_B$ receptor antagonist, is useful to prevent the growth of breast or other solid tumors having $ET_B$ receptors regulating their blood flow.

In addition, because $ET_B$ receptors are vasodilators, it has been found that an $ET_B$ receptor agonist, in combination with a chemotherapeutic agent, is useful in the treatment of a solid tumor, such as those found in breast cancer. In this embodiment, the $ET_B$ receptor agonist more effectively delivers the chemotherapeutic agent to the breast tumor resulting in an enhanced treatment.

Accordingly, one aspect of the present invention is to provide a method of treating solid tumors comprising administering to a mammal in need thereof a therapeutically effective amount of an endothelin agonist and a chemotherapeutic agent.

Another aspect of the present invention is to provide a composition comprising an endothelin agonist, in particular an $ET_B$ agonist. The composition is useful in the treatment of solid tumors. The endothelin agonist is used in conjunction with a chemotherapeutic agent. In particular, the present invention also is directed to compositions containing an endothelin agonist, and to methods of administering the endothelin agonist, in conjunction with a chemotherapeutic agent, to treat solid tumors.

Still another aspect of the present invention is to provide a composition comprising an endothelin agonist, a second therapeutic agent useful in the treatment of a solid tumor, and an excipient.

Still another aspect of the present invention is to provide a method of preventing or treating solid tumors comprising administering to a mammal in need thereof a therapeutically effective amount of an endothelin antagonist. The endothelin antagonist can be an endothelin B antagonist or a mixed endothelin A/B antagonist. Preferably, the endothelin antagonist comprises a specific endothelin B ($ET_B$) antagonist. The endothelin antagonist optionally is used in conjunction with an angiogenesis inhibitor, radiation treatment, or both.

Another aspect of the present invention is to provide a composition comprising an endothelin antagonist, in particular an $ET_B$ antagonist, to an individual in need thereof. The composition is useful in the prevention and treatment of solid tumors.

Another aspect of the present invention is to provide a composition comprising an endothelin antagonist, a second therapeutic agent useful in the prevention or treatment of a solid tumor, and an excipient.

Yet another aspect of the present invention is to provide an article of manufacture for human pharmaceutical use, comprising (a) a container, and (b1) a packaged composition comprising an endothelin agonist and, optionally, (b2) a packaged composition comprising a second therapeutic agent useful in the treatment of a solid tumor, and (c) a package insert containing directions for use of the composition or compositions administered simultaneously or sequentially, in the treatment of a solid tumor. In a preferred embodiment, the endothelin agonist is an $ET_B$ receptor agonist and the second therapeutic agent is a chemotherapeutic agent.

Another aspect of the present invention is to provide an article of manufacture for human pharmaceutical use, comprising (a) a container, (b1) a packaged composition comprising an endothelin antagonist and, optionally, (b2) a packaged composition comprising a second therapeutic agent useful in the treatment of a solid tumor, and (c) a package insert containing directions for use of the composition or compositions, administered simultaneously or sequentially, in the prevention or treatment of a solid tumor. In a preferred embodiment, the endothelin antagonist is an $ET_B$ receptor antagonist, and the second therapeutic agent is an angiogenesis inhibitor, radiation treatment, or both.

These and other novel aspects of the present invention will become apparent from the following detailed description of the preferred embodiments of the invention taken in conjunction with the figures.

DETAILED DESCRIPTION OF THE PREFERRED EMBODIMENTS

Figure 1:
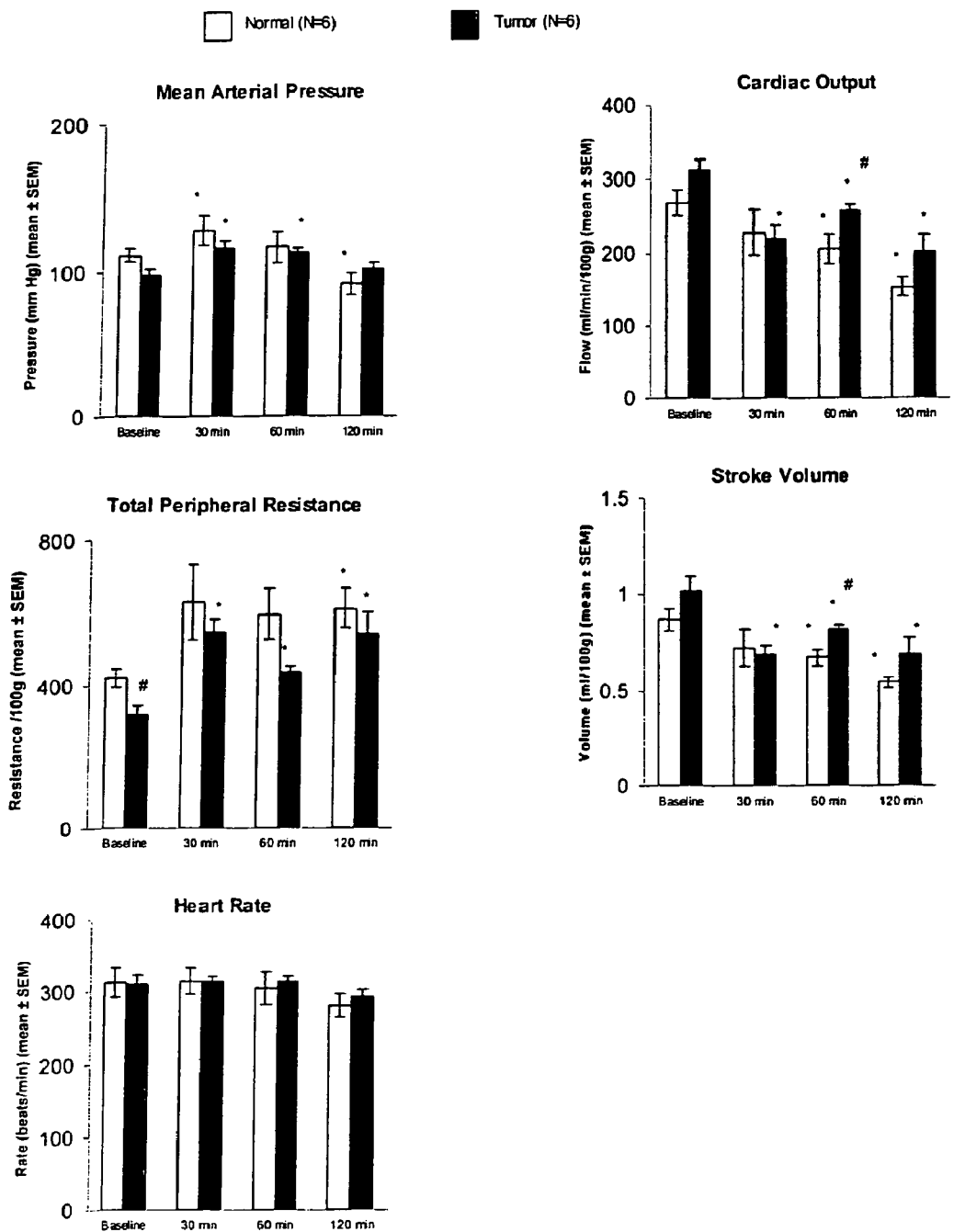
FIG. 1 contains bar graphs showing the effect of ET-1 on systemic hemodynamics of saline-treated and MNU-treated, tumor-bearing rats.

The present invention is directed to compositions and methods of preventing and treating solid tumors, including breast tumors. In particular, the present invention is directed to pharmaceutical compositions comprising either (a) an endothelin agonist and, optionally, a chemotherapeutic agent or (b) an endothelin antagonist, and optionally, angiogenesis inhibitor.

The present invention also is directed to articles of manufacture comprising an endothelin antagonist and an optional angiogenesis inhibitor, packaged separately or together, and an insert having instructions for using these active agents to prevent or treat a solid tumor.

In addition, the present invention is directed articles of manufacture comprising an endothelin agonist and a chemotherapeutic agent, packaged separately or together, and an insert having instructions for using these active agents to treat a solid cancerous tumor.

One method disclosed herein utilizes an endothelin agonist and a chemotherapeutic agent in the treatment of a solid tumor. The agonist and chemotherapeutic agent can be administered in sufficient amounts, simultaneously or sequentially, to achieve the desired therapeutic effect.

Another method disclosed herein utilizes an endothelin antagonist, optionally with an angiogenesis inhibitor, in the treatment of solid tumors. The antagonist and angiogenesis inhibitor can be administered in sufficient amounts, simultaneously or sequentially, to achieve the desired effect.

For the purposes of the invention disclosed herein, the term "treatment" includes preventing, retarding the progression of, shrinking, or eliminating a solid tumor. As such, the term "treatment" includes both medical therapeutic and/or prophylactic administration, as appropriate.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "prodrug" means compounds that transform rapidly in vivo to a compound useful in the invention, for example, by hydrolysis. A thorough discussion of prodrugs is provided in Higuchi et al., *Prodrugs as Novel Delivery Systems*, Vol. 14, of the A.C.S.D. Symposium Series, and in Roche (ed.), *Bioreversible Carriers in Drug Design*, American Pharmaceutical Association and Pergamon Press, 1987.

Endothelin is a vasoactive substance known to modulate blood flow and also has mitogenic properties. Endothelin is present in large concentrations in breast carcinoma tissues compared to normal breast tissue. In accordance with the present invention, it has been shown that a subtype of endothelin receptor ($ET_B$) also is increased in breast cancer. Endothelin acts on $ET_B$ receptors to produce vascular dilation and increase in blood flow to the breast tumor tissue. Importantly, it also has been found that an $ET_B$ receptor antagonist can block the increase in tumor blood flow induced by endothelin.

Because endothelin and $ET_B$ receptors are overexpressed in breast cancer, a selective $ET_B$ receptor antagonist, e.g., BQ788, can be used to block endothelin-induced vasodilation in the breast tumor tissue, and cut off or reduce the blood supply and nutrient supply needed for the breast tumor to grow. An $ET_B$ antagonist can be used alone, or in combination with an angiogenesis inhibitor, like thalidomide, that inhibits the formation of new blood vessels in the tumor tissue. Once the blood supply and nutrient supply to the tumor tissue are reduced, the growth of the tumor also is reduced.

In addition, most chemotherapeutic agents have cytotoxic properties that are targeted to destroy cancer cells, but in the process inflict considerable damage to the body's normal physiological systems. It would be of great advantage, therefore, to selectively deliver chemotherapeutic agents to the tumor tissue. Accordingly, an $ET_B$ receptor agonist that selectively increases blood supply to the tumor can increase the delivery and efficacy of the chemotherapeutic agent. Therefore, $ET_B$ receptor agonists can selectively increase the delivery of chemotherapeutic agents, like tamoxifen, to a breast tumor and increase efficacy of the chemotherapeutic agent.

More particularly, tumor blood supply has become a target of cancer therapy. Several vaso-active substances are known to modulate blood flow including endothelin-1 (ET-1). ET-1 is present in large concentrations in breast carcinoma tissues (i.e., 11.95 pg/mg tissue) compared to normal breast tissue (i.e., 0.12 pg/mg tissue) (Kojima et al., *Surg. Oncol.*, 4(6): 309-315 (1995); Kurbel et al., *Med. Hypotheses*, 52(4):329-333 (1999); Patel et al., *Mol. Cell Endocrinol.*, 126(2):143-151 (1997); Yamashita et al., *Cancer Res.*, 52(14):4046-4049 (1992); Yamashita et al., *Res. Commun. Chem. Pathol. Pharmacol.*, 74(3):363-369 (1991).

Studies have shown that ET-1, ET-3, and $ET_B$ receptor expression is increased in breast cancer (grade III, strong staining compared to negative staining in controls) (Alanen et al., *Histopathology*, 36(2):161-167 (2000)). It also has been found that ET-1 produces an increase in blood flow to the breast tumor by stimulating $ET_B$ receptors. BQ788, an $ET_B$ receptor antagonist, completely blocked ET-1 induced increase in tumor blood flow. Because breast tumor tissue has enhanced $ET_B$ receptor expression, an $ET_B$ receptor antagonist can be used to selectively decrease breast tumor blood supply, and an $ET_B$ receptor agonist can be used to increase blood flow to the breast tumor tissue.

Accordingly, an $ET_B$ receptor agonist in combination with a chemotherapeutic agent decreases breast tumor growth. In addition, an $ET_B$ receptor antagonist, either alone or in combination with an angiogenesis inhibitor, significantly decreases the breast tumor growth.

Administration of an $ET_B$ receptor agonist in combination with a chemotherapeutic agent also can be used to treat or prevent other solid tumors, including, but not limited to, ovarian cancer, colon carcinoma, Kapoli's sarcoma, breast cancer, and melanomas. An endothelin antagonist, alone or in combination with an angiogenesis inhibitor, also can be used in the treatment and prevention of solid tumors.

The following table lists the ET receptor expression for various solid tumors.

| Tumor | ET receptor expression | References |
|---|---|---|
| Ovarian cancer | $ET_A$ and $ET_B$ receptors | Bagnato et al., Cancer Res, 1999, 59, 720-727 |
| Colon carcinoma | $ET_A$ receptors are present in stroma $ET_B$ receptors in endothelium and myofibroblasts | Egidy et al., Am J Pathology, 2000, 157, 1863-1874 |
| Kaposi's sarcoma | $ET_A$ and $ET_B$ receptors in tumor and intratumoral vessels | Bagnato et al., Am J Pathol, 2001, 158, 841-847 |
| Breast cancer | $ET_B$ receptors | Alanen et al., Histopathology: 2000: 36(2): 161 |
| Melanoma | $ET_B$ receptors | Kikuchi et al., Biochem Biophys Res Comm, 1996, 219, 734-739 |

In one embodiment of the present invention, a solid tumor is treated using an endothelin agonist in conjunction with a chemotherapeutic agent. In this method, the endothelin agonist, notably an $ET_B$ agonist, increases blood flow in the breast tumor, which is rich in $ET_B$ receptors. The $ET_B$ agonist, therefore, provides a more selective target for the chemotherapeutic agent and improves the chemotherapeutic effect of the agent.

$ET_B$ agonists useful in the present invention include, but are not limited, to, ET-1, ET-2, ET-3, BQ3020, IRL1620, sarafotoxin S6c, [$Ala^{1, 3, 11, 15}$]ET-1, and mixtures thereof.

It is theorized, but not relied upon herein, that endothelin agonists stimulate $ET_B$ receptors and dilate tumor blood vessels, thereby increasing delivery of the chemotherapeutic agent to the tumor. Endothelin agonists also increase blood perfusion of the solid tumor, and thereby increase oxygenation of the tissue. Improved oxygenation is known to enhance the therapeutic action of chemotherapeutic agents. The mitogenic action of endothelin also can help increase the action of chemotherapeutic agents, when administered together. The mitogenic action of an endothelin agonist can improve incorporation of chemotherapeutic agents in the dividing cells, and increase the efficacy of the chemotherapeutic agents.

In this embodiment, the $ET_B$ agonist is used in conjunction with a chemotherapeutic agent. The $ET_B$ agonist enhances the therapeutic benefit of chemotherapy treatment, including induction chemotherapy and primary (neoadjuvant) chemotherapy. In addition, chemotherapy is frequently indicated as an adjuvant to surgery in the treatment of a cancer. The goal of chemotherapy in the adjuvant setting is to reduce the risk of recurrence and enhance disease-free survival when the primary tumor has been controlled. Chemotherapy is utilized as a treatment adjuvant for a cancer, frequently when the disease is metastatic. An $ET_B$ agonist, therefore, is particularly useful following surgery in the treatment of a solid tumor in combination with chemotherapy.

Chemotherapeutic agents that can be used in the present method include, but are not limited to, alkylating agents, antimetabolites, hormones and antagonists thereof, radioisotopes, antibodies, as well as natural products, and mixtures thereof. For example, an $ET_B$ agonist can be administered with antibiotics, such as doxorubicin and other anthracycline analogs, nitrogen mustards, such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the $ET_B$ agonist can be administered in conjunction with leuprolide or goserelin (synthetic peptide analogs of LH-RH). Examples of chemotherapeutic agents useful in the method of the present invention are listed in the following table.

Alkylating agents
Nitrogen mustards mechlorethamine
cyclophosphamide
ifosfamide
melphalan
chlorambucil
Nitrosoureas carmustine (BCNU)
lomustine (CCNU)
semustine (methyl-CCNU)
Ethylenimine/Methylmelamine thriethylenemelamine (TEM)
triethylene
thiophosphoramide
(thiotepa)
hexamethylmelamine
(HMM, altretamine)
Alkyl sulfonates busulfan
Triazines dacarbazine (DTIC)
Antimetabolites Folic Acid analogs
methotrexate
trimetrexate
Pyrimidine analogs
5-fluorouracil
fluorodeoxyuridine
gemcitabine
cytosine arabinoside
(AraC, cytarabine)
5-azacytidine
2,2'-difluorodeoxycytidine
Purine analogs
6-mercaptopurine
6-thioguanine
azathioprine
2'-deoxycoformycin
(pentostatin)
erythrohydroxynonyladenine
(EHNA)
fludarabine phosphate
2-chlorodeoxyadenosine
(cladribine, 2-CdA)
Type I Topoisomerase Inhibitors camptothecin
topotecan
irinotecan
Natural products
Antimitotic drugs paclitaxel
Vinca alkaloids
vinblastine (VLB)
vincristine
vinorelbine
Taxotere ® (docetaxel)
estramustine
estramustine phosphate -continued Epipodophylotoxins etoposide
teniposide
Antibiotics actimomycin D
daunomycin
(rubidomycin)
doxorubicin
(adriamycin)
mitoxantroneidarubicin
bleomycinsplicamycin
(mithramycin)
mitomycinC
dactinomycin
Enzymes L-asparaginase
Biological response modifiers interferon-alpha
IL-2
G-CSF
GM-CSF
Differentiation Agents retinoic acid
derivatives
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
carboplatin
Anthracenedione mitoxantrone
Substituted urea hydroxyurea
Methylhydrazine derivatives N-methylhydrazine
(MIH)
procarbazine
Adrenocortical suppressant mitotane (o,p'-DDD)
ainoglutethimide
Cytokines interferon (α, β, γ)
interleukin-2
Hormones and antagonists
Adrenocorticosteroids/antagonists prednisone and equivalents
dexamethasone
ainoglutethimide
Progestins hydroxyprogesterone
caproate -continued medroxyprogesterone acetate
megestrol acetate
Estrogens diethylstilbestrol
ethynyl estradiol/
equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines Examples of chemotherapeutic agents that are particularly useful in conjunction with an $ET_B$ agonist include, for example, adriamycin, camptothecin, carboplatin, cisplatin, daunorubicin, doxorubicin, interferon (alpha, beta, gamma), interleukin 2, irinotecan, docetaxel, paclitaxel, topotecan, and therapeutically effective analogs and derivatives of the same.

In another embodiment of the present invention, an endothelin antagonist utilized in the method and composition can be any $ET_B$ receptor antagonist known in the art. $ET_B$ receptors are potent vasodilators. $ET_B$ antagonists inhibit the activity of $ET_B$, and are used to restrict blood flow.

$ET_B$ antagonists useful in the present invention can be selective $ET_B$ antagonists or balanced $ET_A/ET_B$ antagonists. $ET_B$ receptor antagonists, and balanced $ET_A/ET_B$ antagonists, useful in the treatment and/or prevention of solid tumors are set forth in Appendices A through C herein. Additional useful endothelin antagonists can be found in U.S. Patent Application Publication No. US 2002/0082285 A1, incorporated herein by reference.

Examples of $ET_B$ antagonists useful in the present invention include, but are not limited to, atrasentan, tezosentan, bosentan, sitaxsentan, enrasentan, Ro468443, TBC10950, TBC10894, A192621, A308165, SB209670, SB217242, A182086, (s)-Lu302872, J-104132, TAK-044, Sarafotoxin 56c, IRL2500, RES7011, Aselacins A, B, and C, Ro470203, Ro462005, sulfamethoxazole, cochinmicin I, II, and III, L749329, L571281, L754142, J104132, CGS27830, A182086, PD142893, PD143296, PD145065, PD156252, PD159020, PD160672, PD160874, TM-ET-1, IRL3630, Ro485695, L753037, LU224332, PD142893, LU302872, PD145065, Ro610612, SB217242, BQ788, and mixtures thereof. BQ-788 is a preferred specific endothelin B antagonist, and is the sodium salt of N-cis-2,6-dimethylpiperidinocarbonyl-L-gamma-methylleucyl-D-1-methoxycarbonyl triptophanyl-DNle (see *Proc. Natl. Acad. Sci. USA*, 91:4892-4896 (1994)).

In addition to a conventional endothelin antagonist, a compound that inhibits the formation of endogenous endothelin also can be used as the endothelin antagonist in the present invention. Such compounds are useful because they prevent endothelin formation and, therefore, decrease the activity of endothelin receptors. One class of such compounds is the endothelin converting enzyme (ECE) inhibitors. Useful ECE inhibitors include, but are not limited to, CGS34225 (i.e., N-((1-((2-(S)-(acetylthio)-1-oxopentyl)-amino)-1-cyclopentyl)carbonyl-S-4-phenylphenyl-alanine methyl ester) and phosphoramidon (i.e., N-(1-rhamnopyranosyloxyhydroxyphosphinyl)-Leu-Trp).

As discussed more fully hereafter, the $ET_B$ receptor antagonist can be used in conjunction with an angiogenesis inhibitor. As previously stated, angiogenesis is the generation of new vasculature from preexisting blood vessels. An angiogenesis inhibitor retards or eliminates the generation of new vasculature.

Any angiogenesis inhibitor known in the art can be used with an $ET_B$ antagonist in the present method. Examples of angiogenesis inhibitors include, but are not limited to, thalidomide, marimastat, COL-3, BMS-275291, squalamine, 2-ME, SU6668, neovastat, Medi-522, EMD121974, CAI, celecoxib, interleukin-12, IM862, TNP470, avastin, gleevac, herceptin, and mixtures thereof.

In one method of the present invention, wherein an $ET_B$ antagonist and an optional angiogenesis inhibitor are administered to an individual in need thereof to treat a solid tumor by restricting blood flow and inhibiting the formation of new vasculature, the individual also can be treated using radiation therapy and/or a radiosensitizer.

The term "radiosensitizer," as used herein, is defined as a compound administered to a human or other animal in a therapeutically effective amount to increase the sensitivity of cells to electromagnetic radiation and/or to promote the treatment of diseases that are treatable with electromagnetic radiation. Radiosensitizers can be administered in conjunction with an $ET_B$ antagonist and optional angiogenesis inhibitor.

The terms "electromagnetic radiation" and "radiation" as used herein include, but are not limited to, radiation having the wavelength of 10-20 to 100 meters. Preferred embodiments of the present invention employ the electromagnetic radiation of gamma-radiation (10-20 to 10-13 m), X-ray radiation (10-12 to 10-9 m), ultraviolet light (10 nm to 400 nm, visible light (400 nm to 700 nm), infrared radiation (700 nm to 1.0 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include, but are not limited to, hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In summary, the structure, growth, and function of the blood vessels in breast tumors are markedly different from that of normal breast tissue due to changes in the production of growth factors, like vascular endothelial growth factor (VEGF), vasoactive substances like endothelin-1 (ET-1), and cytokines. The role of ET-1 in breast tumor angiogenesis is not adequately understood. Studies have shown that the expression of proET-1, proET-3, and $ET_B$ receptors is increased in breast tumor. However, it is unclear whether there is any change in ET-1 induced vascular responses in the breast tumor. Hence, the systemic hemodynamics and regional circulatory effects of ET-1 in rats with breast tumors was investigated.

For the first time, it has been demonstrated that ET-1 produces an increase in blood flow to the breast tumor by stimulating $ET_B$ receptors. BQ788, an $ET_B$ receptor antagonist, completely blocked an ET-1 induced increase in tumor blood flow. Because breast tumor tissue has enhanced $ET_B$ receptor expression, an $ET_B$ receptor antagonist can be used to decrease blood supply selectively to tumor tissue.

Similarly, an $ET_B$ receptor agonist increases blood supply to tumor tissue, thereby facilitating administration of a chemotherapeutic drug to the tumor. Accordingly, an $ET_B$ receptor agonist can be used in combination with a chemotherapeutic agent in the treatment of a solid tumor, like a breast tissue. In addition, most chemotherapeutic agents have cytotoxic properties and are targeted to destroying cancer cells. However, in the process, chemotherapeutic agents inflict considerable damage to the body's normal physiological systems. $ET_B$ receptor agonists that selectively increase blood supply to the tumor therefore can increase the delivery and efficacy of chemotherapeutic agents.

$ET_B$ receptor antagonists can be used in the treatment of a breast cancer either alone or in combination with an angiogenesis inhibitor. Angiogenesis inhibitors prevent the formation of new blood vessels needed for the growth of the tumor. Therefore, a combination of an angiogenesis inhibitor with an $ET_B$ receptor antagonist, which selectively decreases the blood supply to breast tumor tissue, significantly decreases tumor growth.

Therefore, an $ET_B$ receptor agonist in combination with a chemotherapeutic agent decreases solid tumor growth. In addition, an $ET_B$ receptor antagonist, either alone or in combination with an angiogenesis inhibitor, significantly decreases solid tumor growth.

Materials and Methods

Animals

Female Sprague Dawley rats (Harlan Co., Madison, Wis.) weighing 180-200 grams (g) were used. All animals were housed, three to a cage, in a temperature controlled room (23±1° C.), humidity (50±10%), and artificial light (0600-1800 hr). The animals were given food and water ad libitum. The experiments were conducted after the animals had been acclimatized to the environment for at least four days.

Drugs

N-methylnitrosourea (MNU) was purchased from Ash Stevens Inc., Detroit, Mich. BQ788 (N-cis-2,6-dimethylpiperidinocarbonyl-L-gamma-methyl-leucyl-D-1-methoxycarbonyltrptophanyl-D-Nle), IRL1620, and Endothelin-1 (ET-1) were obtained from American Peptide Company Inc., Sunnyvale, Calif. BQ788 was dissolved in saline and ET-1 was dissolved in 0.1% albumin.

Methods for Effect of IRL1620 and Taxol on Breast Tumor Perfusion

MNU (50 mg/kg, i.p.) or saline (1 ml/kg, i.p.) was administered to female Sprague Dawley rats. After the tumors reached 2-4 cm in diameter, the blood flow experiments were performed. The animals were divided into the following groups:

(i) Saline injection followed by taxol (3 mg/kg) after 15 minutes in normal rats (N=4);

(ii) IRL 1620 (3 nmol/kg) injection followed by taxol (3 mg/kg) after 15 minutes in normal rats (N=4);

(iii) Saline injection followed by taxol (3 mg/kg) after 15 minutes in tumor bearing rats (N=4); and (iv) IRL 1620 (3 nmol/kg) injection followed by taxol (3 mg/kg) after 15 minutes in tumor bearing rats (N=4).

Surgical Preparations

Rats were anesthetized with urethane (1.5 g/kg, i.p.) (Sigma Chemicals, St. Louis, Mo.). The left femoral vein was cannulated (PE 50 tubing, Clay Adams, Parsipanny, N.J.) for drug administration. The left femoral artery was cannulated, and was used for withdrawal of reference blood samples. The right femoral artery was cannulated and connected to a Gould P23 ID pressure transducer for recording the blood pressure on a Grass P7D polygraph (Grass Instrument Co., Quincy, Mass., USA) through a 7PI preamplifier. The heart rate (HR) was recorded through a 7P4B Grass tachograph (Grass Instrument Co., Quincy, Mass.) triggered from blood pressure signals.

Breast Blood Perfusion Measurement by Laser Doppler Flowmetry (LDF)

The blood perfusion to the mammary gland of the rats was measured using laser Doppler flowmetry. The animals were shaved around the nipples and the skin surrounding the mammary glands was dissected out. A standard model fiber optic probe was secured to the mammary artery and connected to a Periflux PF2b 4000 Laser Doppler Flowmetry (Perimed KB, Stockholm, Sweden). The time constant was set to 1.5 seconds, and the band width was set to 4 KHz.

Statistical Analysis

All data are presented as mean±SEM. Data were analyzed using analysis of variance followed by Duncan's test. A level of $p<0.05$ was considered significant.

Results

Effect of IRL1620 and Taxol on Breast Tumor Perfusion

Figure 5:
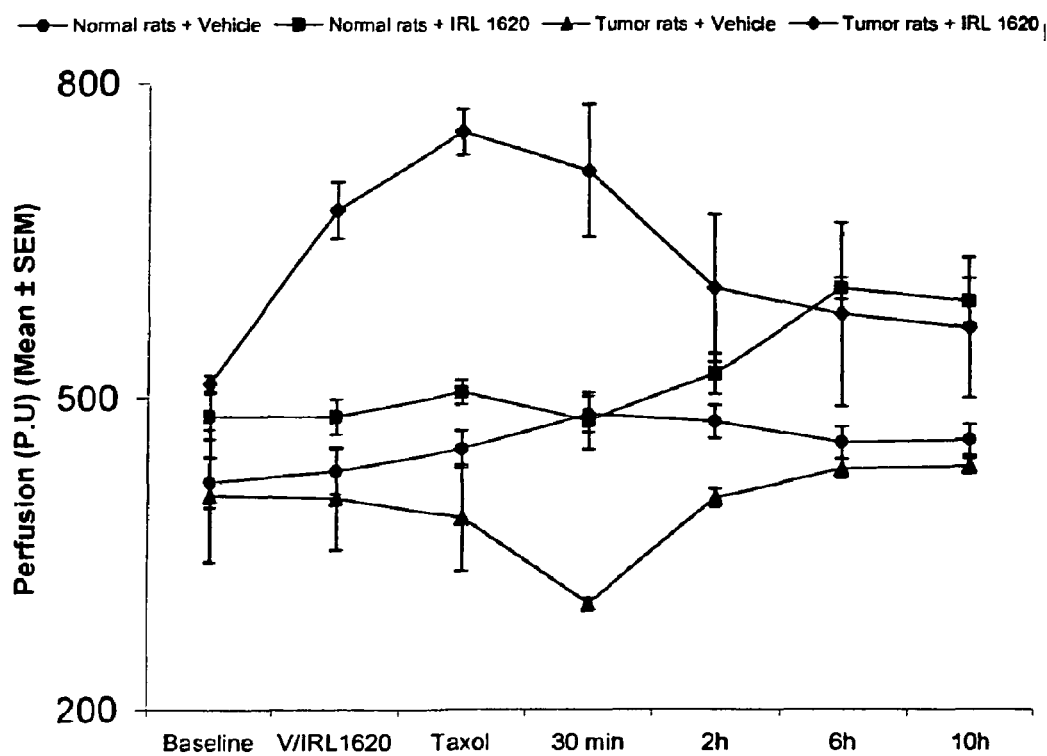
FIG. 5 contains plots showing the effect of IRL1620 on paclitaxel-induced changes in tumor perfusion.

No change in blood flow to the breast tissue of normal rats was observed following the administration of saline or IRL1620 and taxol. Significant differences were observed between the blood flow in the tumor tissue after IRL1620 injection (36.3%, $p<0.05$) and after taxol administration (51.9%, $p<0.0-5$) from baseline (see FIG. 5).

Effect of IRL 1620 and Taxol on Blood Pressure

No change in blood pressure was observed following the administration of saline or IRL 1620 and taxol in normal and tumor bearing rats.

Experimental Protocol for ET-1 Infusion into Rats

The following groups of animals were studied to evaluate the effect of ET-1 infusion on systemic hemodynamics and blood flow to the mammary tissue of normal and tumor-bearing rats.

(i) ET-1 (50 ng/kg/min) infusion for 30 minutes in rats treated with saline (N=6); and (ii) ET-1 (50 ng/kg/min) infusion for 30 minutes in treated with MNU (50 mg/kg, i.p.) (N=6).

The following groups were studied to evaluate the role of $ET_B$ receptors on the changes induced by ET-1 infusion on the systemic hemodynamics and blood flow to the mammary tissue of normal rats and rats with breast tumors:

(i) BQ788 (0.5 µmol/kg) infusion for 20 minutes followed by ET-1 (50 ng/kg/min) infusion for 30 minutes in rats treated with saline (N=5);

(ii) BQ788 (0.5 µmol/kg) infusion for 20 minutes followed by ET-1 (50 ng/kg/min) infusion for 30 minutes in rats treated with MNU (50 mg/kg, i.p.) (N=5).

MNU and saline treatments were performed as intraperitoneal (i.p.) injections three months prior to the study. Rats were palpated regularly starting four weeks after the treatments. Once tumors reached an optimal size (i.e., 4-8 mm in diameter), the experiments were initiated. Systemic hemodynamic and regional circulation parameters were determined at baseline, 30, 60, and 120 minutes after starting ET-1 (50 ng/kg/min) infusion. Because ET-1 infusion was performed for 30 minutes, the 30-minute data shows the effect of ET-1, and the 60- and 120-minute data indicates duration of the ET-1 effect.

Surgical Preparations

Rats were anesthetized with urethane (1.5 g/kg, i.p.) (Sigma Chemicals, St. Louis, Mo.). All surgical areas were shaved and cleaned with alcohol swabs. The left femoral vein was cannulated (PE 50 tubing, Clay Adams, Parsipanny, N.J.) for drug administration. The left femoral artery was cannulated (PE 50 tubing) and was used for withdrawal of reference blood sample in microsphere studies using a withdrawal pump (Model 22, Harvard Apparatus, South Natick, Mass.). The right femoral artery was cannulated (PE 50 tubing) and connected to a Gould P23 ID pressure transducer for recording the blood pressure on a Grass P7D polygraph (Grass Instrument Co., Quincy, Mass., USA) through a 7PI preamplifier. The heart rate (HR) was recorded through a 7P4B Grass tachograph (Grass Instrument Co., Quincy, Mass.) triggered from blood pressure signals. The right carotid artery was exposed and a PE 50 tubing was guided through the common carotid artery into the left ventricle. The presence of the cannula in the left ventricle was confirmed by recording the pressure on the Grass polygraph using the Statham P23 DC pressure transducer (Grass Instrument Co., Quincy, Mass.). When the cannula reached the left ventricle, the diastolic pressure dropped to zero. In order to maintain the blood $pO_2$, $pCO_2$, and pH constant, and to avoid the effect of respiration on blood pressure and HR, animals were kept on constant rate artificial respiration by inserting an endotracheal cannula connected to a rodent ventilator (Model 683, Harvard Apparatus Inc., South Natick, Mass.).

Determination of Systemic Hemodynamics and Regional Circulation

Systemic hemodynamics and regional blood circulation were determined using a literature described procedure (13, 16, 47). At each measurement, a thoroughly mixed suspension of approximately 100,000 microspheres (15±1 μm diameter) labeled with $^{46}Sc$ (scandium), $^{113}Sn$ (tin), $^{141}Ce$ (cerium), or $^{95}Nb$ (niobium) (New England Nuclear Corporation, Boston, Mass., USA) in 0.2 ml saline were injected into the left ventricle and flushed with 0.3 ml saline over a 15 second period. In order to calculate blood flow, arterial blood was withdrawn at a rate of 0.5 ml/min through the right femoral artery. Blood was withdrawn for 90 seconds starting about 5-10 seconds before microsphere injection. At the end of the experiment, the animals were sacrificed with an overdose of pentobarbital sodium. All tissues and organs were dissected out, weighed, and placed in vials. The radioactivity in the standards, the blood samples, and the tissue samples were counted in a Packard Minaxi Auto-Gamma 5000 series gamma counter (Packard Instruments Co., Downers Grove, Ill.) with preset windows discriminating the isotope energies. The following parameters were calculated: (1) cardiac output (CO) ((radioactivity injected×withdrawal rate of arterial blood)/radioactivity in sampled arterial blood), (2) stroke volume (SV) (CO/HR), (3) total peripheral resistance (TPR) (mean arterial pressure (MAP)/CO), (4) regional blood flow ((radioactivity in tissue×withdrawal rate of arterial blood)/radioactivity in sampled arterial blood), and (5) regional vascular resistance (MAP/regional blood flow). The data were calculated using computer programs described in the literature (45).

Breast Blood Perfusion Measurement by Laser Doppler Flowmetry (LDF)

Blood perfusion to the mammary gland of the rats was measured using laser Doppler flowmetry as described in literature procedures (50, 51). The animals were shaved around the nipples. The skin surrounding the mammary glands was dissected out as a lambeau about 6 cm wide and 4 cm long. A standard model fiber optic probe was applied to the surface of the lambeau, and secured to the tissue by double stick tape. The lambeau was placed in a metal holder and taped down to prevent movement, then connected to a Periflux PF2b 4000 Laser Doppler Flowmetry (Perimed KB, Stockholm, Sweden). The time constant was set at 1.5 seconds and the bandwidth was set at 4 KHz.

Statistical Analysis

All data are presented as mean±SEM. Data were analyzed using analysis of variance followed by Duncan's test. A level of $p<0.05$ was considered significant.

Results

Effect of ET-1 on Systemic Hemodynamics in Normal and Tumor-Bearing Rats

The baseline systemic hemodynamic parameters in normal (saline treated) rats were MAP: 111.1±4.8 mmHg; CO: 268.6±17.6 ml/min; SV: 0.87±0.06 ml; TPR: 419.6±24.37 mmHg·min/ml; and HR: 312.5±20.2 beats/min. In normal rats, a significant increase in MAP was observed at 30 minutes (14.5%; $p<0.05$), and a decrease at 120 minutes (17.8%; $p<0.05$) following ET-1 infusion. TPR increased at 120 minutes (49.2%; $p<0.05$). CO decreased at 60 and 120 minutes (22.9% and 42.5% respectively; $p<0.05$) after ET-1 infusion. SV decreased at 60 and 120 minutes (20.9% and 36% respectively; $p<0.05$). No significant change in HR was observed (FIG. 1).

The baseline systemic hemodynamic parameters in tumor-bearing (MNU treated) rats were similar to that in normal rats. A significant increase in MAP was observed at 30 minutes (19.1%; $p<0.05$) and at 60 minutes (15.3%; $p<0.05$) following ET-1 infusion in tumor-bearing rats. TPR increased at 30 minutes (73.9%; $p<0.05$), 60 minutes (39.7%; $p<0.05$), and 120 minutes (71.4%; $p<0.05$) following administration of ET-1. CO decreased at 30, 60 and 120 minutes (29.4%, 16.7% and 36.1% respectively; $p<0.05$). SV decreased significantly at 30, 60 and 120 minutes (31.1%, 17.9% and 32.1% respectively; $p<0.05$). No change in HR was observed (FIG. 1).

Figure 2:
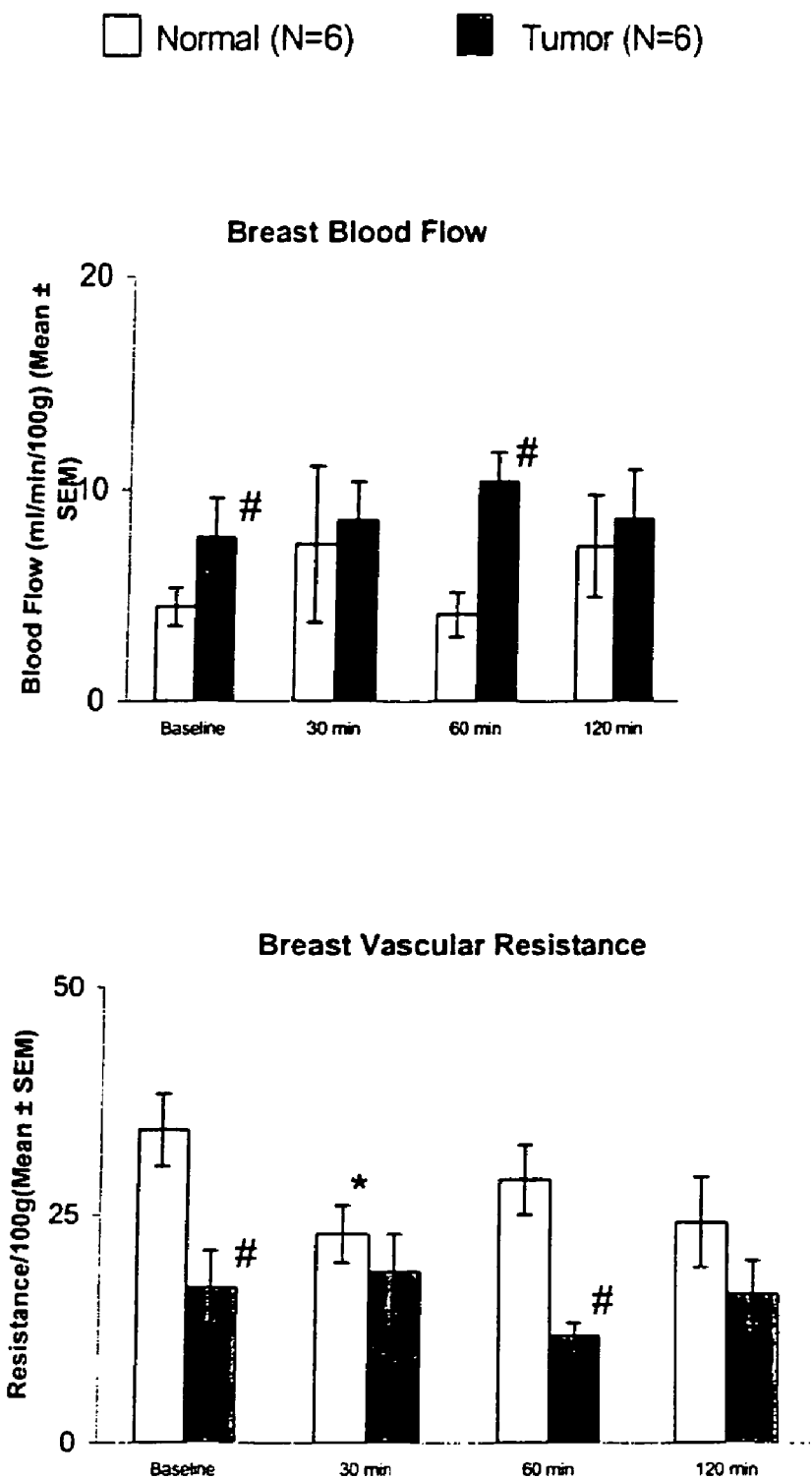
FIG. 2 contains bar graphs showing the effect of ET-1 on blood flow and regional vascular resistance in the breast tissue of saline-treated and MNU-treated rats.

Effect of ET-1 on Regional Blood Flow and Vascular Resistance in the Breast Tissue of Normal and Tumor-Bearing Rats No change in blood flow to the breast tissue of normal saline-treated rats was observed following the administration of ET-1. A significant decrease (18.61%; $p<0.05$) in vascular resistance at 60 minutes was observed, which is 30 minutes post ET-1 infusion, in the breast tissue of normal rats (FIG. 2).

Significant differences were observed between the blood flow and the regional vascular resistance in the breast tissue of tumor-bearing (MNU treated) and normal (saline treated) rats. A significant increase (153%; $p<0.05$) in blood flow to the breast tissue of tumor-bearing rats as compared to normal rats was observed at 60 minutes following administration of ET-1. The vascular resistance in the tumor-bearing rats was significantly different at baseline (102%; $p<0.05$) and at 60 minutes (147%; $p<0.05$) following ET-1 administration compared to normal rats.

Figure 3:
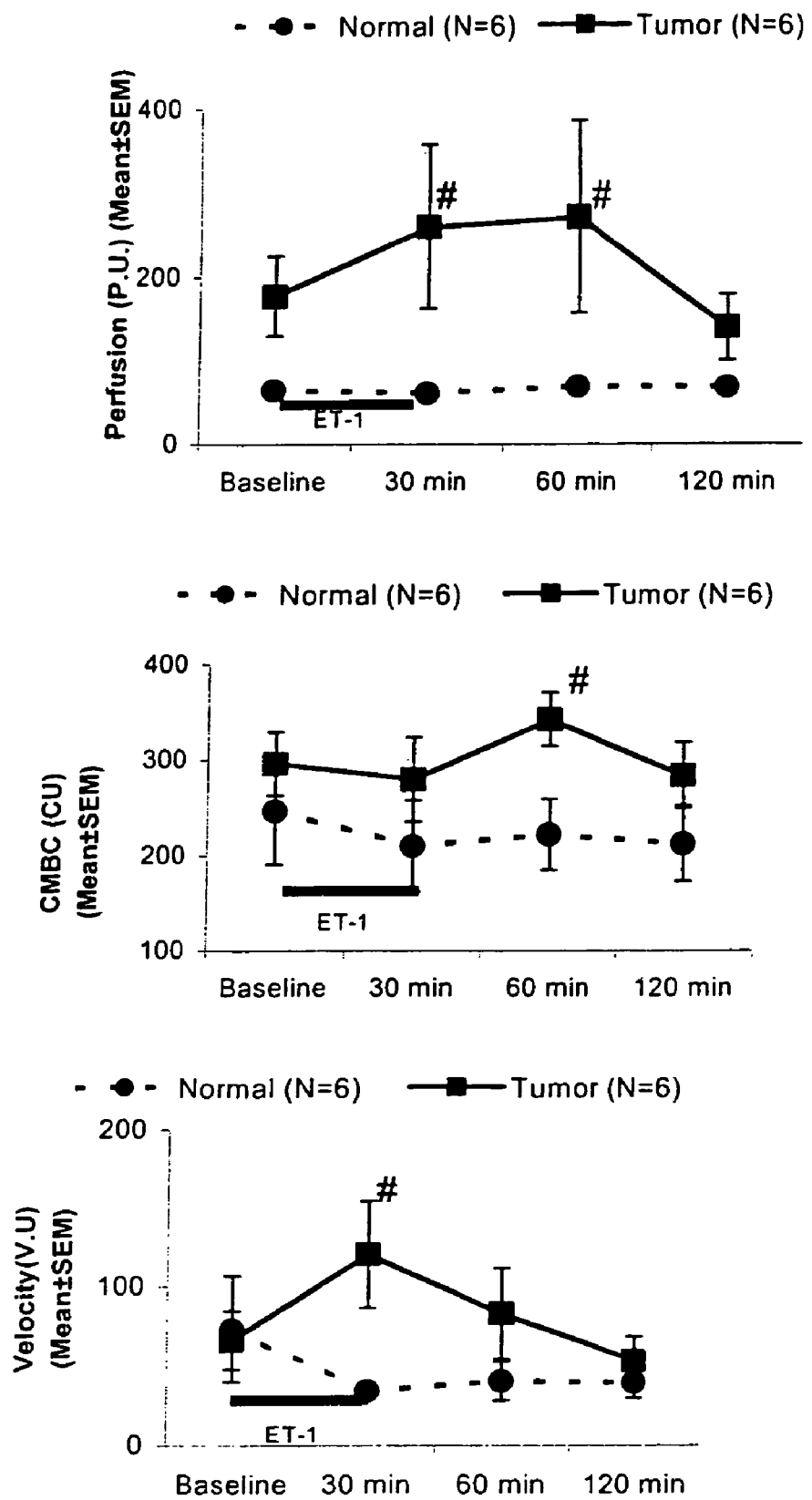
FIG. 3 contains plots showing the effect of ET-1 on perfusion, CMBC, and velocity of blood cells in breast tissue of saline-treated and tumor tissue of MNU-treated rats.

Effect of ET-1 on Blood Perfusion in the Breast Tissue of Normal and Tumor-Bearing Rats as Measured by LDF FIG. 3 shows the changes in perfusion, concentration of moving blood cells (CMBC), and velocity of red blood cells (RBC) in the breast tissue of tumor-bearing and normal rats. Blood perfusion in the breast tissue of normal rats did not change after ET-1 administration. Perfusion in the breast tissue of tumor-bearing rats at 30 minutes following ET-1 administration increased significantly (176%; p<0.05) compared to normal rats. This increase in perfusion returned to baseline at 60 and 120 minutes following ET-1 administration in tumor-bearing rats.

The CMBC in tumor-bearing rats increased significantly (54%; p<0.05) at 60 minutes post ET-1 administration as compared to normal rats. CMBC returned to baseline at 120 minutes after ET-1 administration. The velocity of RBC increased significantly (252%; p<0.05) at 30 minutes post ET-1 administration compared to normal rats. Two hours (120 minutes) after ET-1 administration, the velocity of RBC in tumor-bearing rats returned to baseline.

Figure 4:
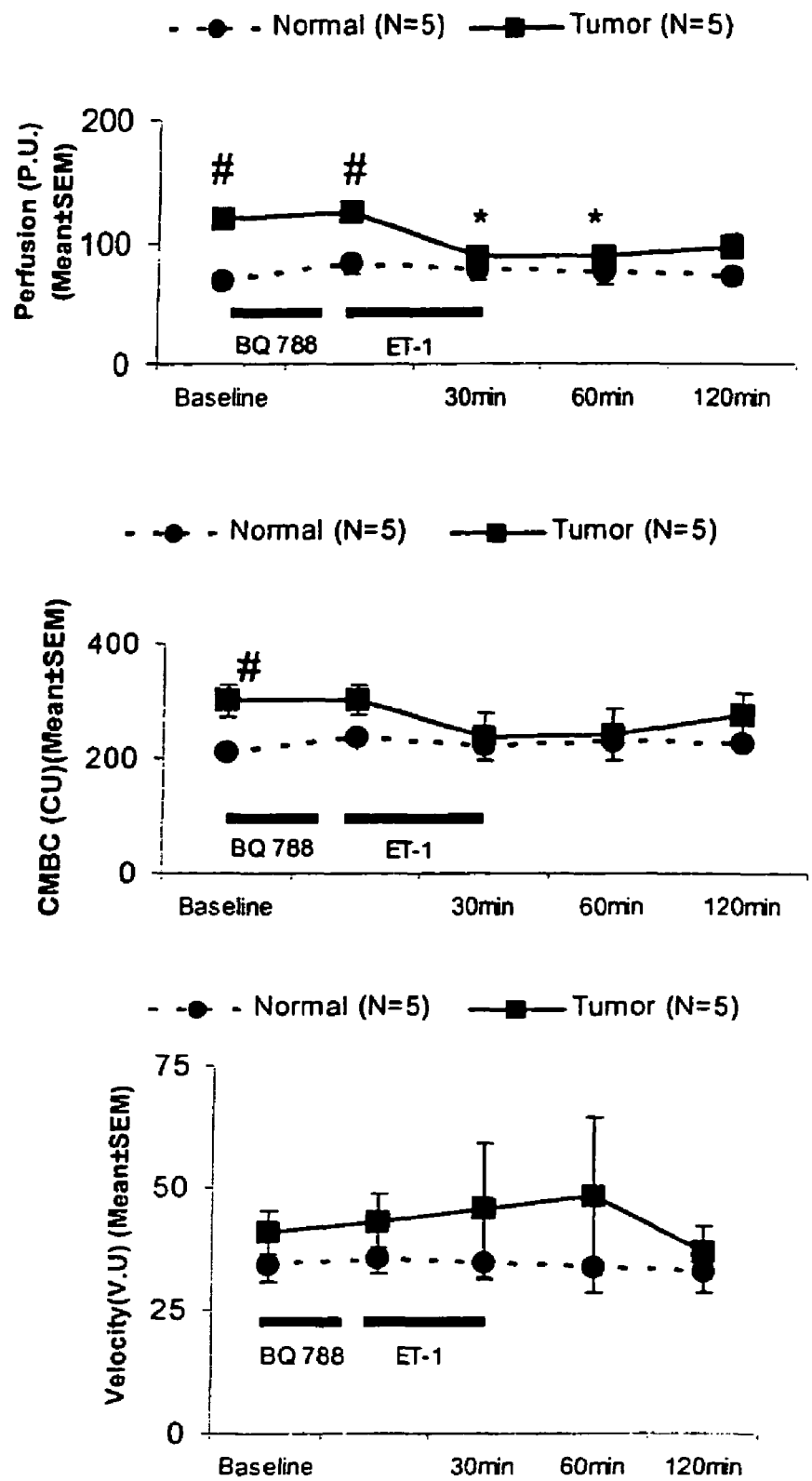
FIG. 4 contains plots showing the effect of BQ788 on ET-1-induced changes in blood perfusion, CMBC, and velocity of blood cells in breast tissue of saline-treated and tumor tissue of MNU-treated rats.

Effect of BQ788 on ET-1 Induced Changes in Blood Perfusion in the Breast Tissue of Normal and Tumor-Bearing Rats as Measured by LDF FIG. 4 shows the effect of BQ788 on changes induced by ET-1 in blood perfusion, CMBC, and velocity of RBC in tumor-bearing and normal rats, respectively. Blood perfusion in the breast tissue of normal rats did not change significantly after BQ788 administration or ET-1 infusion. However, perfusion in the breast tumor tissue of tumor-bearing rats decreased significantly at 30 (25.25±5.7%; P<0.05) and 60 minutes (25.17±2.8%; P<0.05) following ET-1 infusion in BQ788 pretreated rats. Pretreatment with BQ788 attenuated the increase in perfusion induced by ET-1 in tumor-bearing rats. No difference between the perfusion in breast tissue of tumor-bearing rats and normal rats was observed following ET-1 administration in BQ788 pretreated rats.

The baseline CMBC in tumor-bearing rats was significantly higher than the baseline CMBC of breast tissue of normal rats (42.4%; P<0.05). However, after BQ788 infusion, no difference between CMBC of tumor-bearing and normal rats was observed. In addition, no difference in velocity of RBC between the two groups was observed.

The above tests show the effect of ET-1 on systemic hemodynamics and blood flow to the breast tissue of saline-treated and MNU-treated tumor-bearing rats. It is known that ET-1 stimulates angiogenesis by promoting production of VEGF. Studies have shown that ET-1 is increased in many cancer tissues like breast carcinoma (60), breast phyllode tumor (59), prostate carcinoma (31), liver carcinoma (21), and some meningiomas (33). The above tests demonstrate changes in ET-1-induced vascular responses in the breast tumor. The method used in these tests was a well-established radioactive microsphere technique to study the systemic hemodynamics and regional blood circulation (12-15).

ET-1 is a powerful vasoconstrictor (61). ET-1 belongs to a family of peptides approximately 21 amino acids long. At least three forms of ET receptors exist, and are known as $ET_A$, $ET_B$, and $ET_C$. $ET_A$ has a higher affinity for ET-1, but $ET_B$ has equal affinity for both ET-1 and ET-3 (2, 17, 42). ET-1 has complex cardiovascular effects. When administered to anesthetized and ventilated rats, an immediate decrease followed by a sustained increase in blood pressure is observed (22). It has been found that $ET_A$ receptors are responsible for the vasoconstrictor responses, and $ET_B$ receptors are responsible for the vasodilatory actions of ET-1. ET-1 administration resulted in an increase in blood flow to the skin tumors possibly due to the vasodilatory actions of $ET_B$ (6). Similar results in blood flow to the breast tumor of rats are expected because of an increase in ET-1 and $ET_B$ in breast tumors.

Infusion of 50 ng/kg/min of ET-1 caused a biphasic response in blood pressure, i.e., an immediate but short lasting decrease followed by a sustained increase. These results are in accordance with previous studies (20, 30, 38, 56). ET-1 produced a marked pressor response in both normal and tumor-bearing rats, which was accompanied by a significant decrease in SV and CO. TPR significantly increased in both normal and tumor-bearing rats and may explain the observed pressor response.

Baseline blood flow to the breast tumor tissue of tumor-bearing rats was higher than blood flow in normal animals. This was observed in an earlier study and is theorized, but not relied upon, as being attributed to the recruitment of new blood vessels in the tumor (55). Blood flow to the breast tumor following ET-1 administration was significantly increased as compared to that observed in the breast tissue of normal rats. Laser Doppler flowmetry showing an increase in blood perfusion to the breast tumor confirmed an increase in blood flow observed in the breast tumor tissue following ET-1 administration. The increase in blood perfusion is theorized, but not relied upon, as being attributed to an increase in either velocity of RBC velocity or CMBC, or both. At the end of ET-1 infusion an increase in velocity of RBC was observed, whereas an increase in CMBC was observed 30 minutes after ET-1 infusion.

Further, the observed increase in blood flow in response to ET-1 is theorized, but not relied upon, as being attributed to $ET_B$ mediated vasodilation. Studies have shown that ET-1 and $ET_B$ receptor expression is augmented in the breast cancer tissue (1, 60). In accordance with the present invention, it was found that administration of BQ788 blocked the ET-1-induced increase in blood flow to the tumor tissue. BQ788 (i.e., N-cis-2,6-dimethylpiperidinocarbonyl-L-gamma-methylleucyl-D-1-methoxycarbonyltrptophanyl-D-Nle) is a specific $ET_B$ receptor antagonist. BQ788 inhibits binding to $ET_B$ receptors with an $IC_{50}$ value of 1.2 nM.

BQ788 was used to determine the role of $ET_B$ receptors in ET-1 induced vasodilation in the breast tumor. This result suggests that ET-1-induced vasodilatory responses are mediated through $ET_B$ receptors. Expression of $ET_B$ receptors is significantly higher in the endothelial cells than in the smooth muscle cells, and is regulated by various growth factors and cytokines (49). Normal breast tissue has a higher level of $ET_B$ than $ET_A$ receptors (1), and it is theorized, but not relied upon, that during breast cancer, $ET_B$ receptors are overexpressed and contribute to maintaining blood flow to the tumor tissue.

As tumors grow, new blood vessels are recruited to supply nutrients. This recruitment can be incorporation of existing vessels into the tumor or creation of new blood vessels (7). Studies have shown that new vessels have different physical properties than normal vasculature. Unlike normal vessels, these vessels do not have any smooth muscle layers or any innervation, but consist only of single layers of endothelial cells.

In summary, the present tests clearly demonstrate that the infusion of ET-1 produced an increase in blood flow and a decrease in vascular resistance of the breast tumor tissue, and that this increase in blood flow can be blocked by an $ET_B$ receptor antagonist, e.g., BQ788.

The increased blood flow observed in the rat breast tumor is attributed to increased $ET_B$ receptors. Therefore, blocking these receptors can reduce blood flow to the tumor. The clinical significance of these findings is that $ET_B$ receptor antagonists play a role in reducing blood supply to the breast tumor tissue, and thereby prevent and/or reduce growth of the breast tumor, and solid tumors in general.

The test results, therefore, clearly demonstrate that $ET_B$ antagonists, like BQ788, can prevent or treat solid tumors. $ET_B$ antagonists optionally can be combined with an angiogenesis inhibitor to potentiate the effects of the $ET_B$ antagonist.

The $ET_B$ antagonist, optional angiogenesis inhibitor, $ET_B$ agonist, and chemotherapeutic agent (hereafter collectively "active ingredients") can be formulated in suitable excipients for oral administration or for parenteral administration. Such excipients are well known in the art. The active ingredients typically are present in such a composition in an amount of about 0.1% to about 75% by weight.

Pharmaceutical compositions containing the active ingredients are suitable for administration to humans or other mammals. Typically, the pharmaceutical compositions are sterile, and contain no toxic, carcinogenic, or mutagenic compounds that would cause an adverse reaction when administered. Administration of the pharmaceutical composition can be performed before, during, or after the onset of solid tumor growth.

A method of the present invention can be accomplished using active ingredients as described above, or as a physiologically acceptable salt, derivative, prodrug, or solvate thereof. The active ingredients can be administered as the neat compound, or as a pharmaceutical composition containing either or both entities.

The active ingredients can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

The pharmaceutical compositions include those wherein the active ingredients are administered in an effective amount to achieve their intended purpose. More specifically, a "therapeutically effective amount" means an amount effective to prevent development of, to eliminate, to retard the progression of, or to reduce the size of a solid tumor. Determination of a therapeutically effective amount is well within the capability of those skilled in the art, especially in light of the detailed disclosure provided herein.

A "therapeutically effective dose" refers to that amount of the active ingredients that results in achieving the desired effect. Toxicity and therapeutic efficacy of such active ingredients can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amount and interval can be adjusted individually to provide levels of the active ingredients that are sufficient to maintain therapeutic or prophylactic effects.

The amount of pharmaceutical composition administered is dependent on the subject being treated, on the subject's weight, the severity of the affliction, the manner of administration, and the judgment of the prescribing physician.

Specifically, for administration to a human in the curative or prophylactic treatment of a breast tumor, oral dosages of active ingredients, individually generally are about 10 to about 200 mg daily for an average adult patient (70 kg), typically divided into two to three doses per day. Thus, for a typical adult patient, individual tablets or capsules contain about 0.1 to about 50 mg active ingredients, in a suitable pharmaceutically acceptable able vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The active ingredients can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active ingredients are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active ingredients, and preferably from about 25% to about 90% active ingredients. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active ingredients, and preferably about 1% to about 50% of active ingredients.

When a therapeutically effective amount of the active ingredients is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to an isotonic vehicle.

Suitable active ingredients can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active ingredients with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active ingredients can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the active ingredients can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active ingredients also can be formulated in rectal compositions, such as suppositories or retention enemas, e.g., containing conventional suppository bases. In addition to the formulations described previously, the active ingredients also can be formulated as a depot preparation. Such long-acting formulations can be administered by implantation (for example, subcutaneously or intramuscularly) or by intramuscular injection. Thus, for example, the active ingredients can be formulated with suitable polymeric or hydrophobic materials (for example, as an emulsion in an acceptable oil) or ion exchange resins, or as sparingly soluble derivatives, for example, as a sparingly soluble salt.

In particular, the active ingredients can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The active ingredients also can be injected parenterally, for example, intravenously, intramuscularly, subcutaneously, or intracoronarily. For parenteral administration, the active ingredients are best used in the form of a sterile aqueous solution which can contain other substances, for example, salts, or monosaccharides, such as mannitol or glucose, to make the solution isotonic with blood.

For veterinary use, the active ingredients are administered as a suitably acceptable formulation in accordance with normal veterinary practice. The veterinarian can readily determine the dosing regimen and route of administration that is most appropriate for a particular animal.

As stated above, it has been discovered that using an $ET_B$ antagonist, alone or together with an angiogenesis inhibitor, is useful in the treatment and prevention of solid tumors.

The angiogenesis inhibitor, like the $ET_B$ antagonist, is administered in an effective amount to perform its intended function. The angiogenesis inhibitor can be administered by any suitable means, typically using a composition containing the angiogenesis inhibitor.

The angiogenesis inhibitor can be administered simultaneously with the $ET_B$ antagonist, or prior to or after $ET_B$ antagonist administration. The $ET_B$ antagonist and optional angiogenesis inhibitor also can be administered in conjunction with radiation treatment of the solid tumor and an optional radiosensitizer.

In another embodiment, the solid tumor can be treated by administration of therapeutically effective amounts of an $ET_B$ agonist and a chemotherapeutic agent. Administration of the $ET_B$ agonist and chemotherapeutic agent can be performed as described above for the $ET_B$ antagonist and angiogenesis inhibitor.

REFERENCES

1. K. Alanen et al., *Histopathology*, 36:161 (2000).
2. H. Arai et al., *Nature*, 348:730 (1990).
3. T. Asano et al., *J. Neurooncol*, 18:1 (1994).
4. E. B. Astwood et al., *Am J. Anat.*, 61 (1937).
5. P. A. Baley et al., *J. Clin. Invest*, 85:1320 (1990).
6. K. M. Bell et al., *J. Cardiovasc. Pharmacol.*, 26:s222 (1995).
7. D. J. Chaplin et al., *Semin. Radiat. Oncol.*, 8:151 (1998).
8. A. Cruz et al., *J. Vasc. Res.*, 38:536 (2001).
9. T. L. Dao et al., *J. Natl. Cancer Inst.*, 71:201 (1983).
10. J. Folkman, *Cancer Res.*, 46:467 (1986).
11. K. Goto, *Biol. Pharm. Bull.*, 24:1219 (2001).
12. A. Gulati et al., *Am J. Physiol.*, 273:H827 (1997).
13. A. Gulati et al., *Life Sci.*, 55:827 (1994).
14. A. Gulati et al., *Crit. Care Med.*, 24:137 (1996).
15. A. Gulati et al., *J. Lab. Clin. Med.*, 126:559 (1995).
16. A. Gulati et al., *Alcohol*, 6:9 (1989).
17. S. Hori et al., *Endocrinology*, 130:1885 (1992).
18. C. Huggins et al., *Proc Natl Acad Sci* USA 45:1294 (1959)
19. C. Huggins et al., *Science*, 137 (1962).
20. A. Inoue et al., *Proc Natl Acad Sci* USA 86:2863 (1989).
21. S. Kar et al., *Biochem Biophys Res Commun* 216:514 (1995).
22. T. Kuwaki et al., *Jpn J Physiol*, 40:827 (1990).
23. P. Lissoni et al., *J Biol Regul Homeost Agents*, 15:140 (2001).
24. T. F. Luscher et al., The endothelium: modulator of cardiovascular function, CRC Press, Boca Raton, pg. 61 (1990).
25. D. Macejova et al., *Endocr Regul*, 35:53 (2001).
26. A. Matsuura et al., *Hypertension*, 32:89 (1998).
27. T. Matsuura et al., *Br J Pharmacol*, 122:81 (1997).
28. T. Matsuura et al., *Jpn J Pharmacol*, 71:213 (1996).
29. J. Mattsson et al., Tumor vessel innervation and influence of vasoactive drugs on tumor blood flow. In, *Tumor Blood Circulation*, CRC Press, Boca Raton, pg. 129 (1979).
30. T. Miyauchi et al., *Hypertension*, 14:427 (1989).
31. J. B. Nelson et al., *Cancer Res*, 56:663 (1996).
32. Y. Okuda et al., *Life Sci*, 63:477 (1998).
33. U. Pagotto et al., *J Clin Invest*, 96:2017 (1995).
34. K. V. Patel et al., *Cancer Treat Res*, 83:369 (1996).
35. A. Pedram et al., *J Biol Chem*, 272:17097 (1997).
36. H. S. Reinhold, In vivo observations of tumor blood flow. In, *Tumor Blood Circulation*, CRC Press, Boca Raton, pg. 115 (1979).
37. A. E. Rogers et al., Chemically induced mammary gland tumors in rats: modulation by dietary fat. Alan R. Liss, Inc., New York 255 (1996).
38. P. Rohmeiss et al., *Am J Physiol*, 258:H337 (1990).
39. I. H. Russo et al., *J Natl Cancer Inst*. 61:1439 (1978).
40. J. Russo et al., *Lab Invest*, 62:244 (1990).
41. J. Russo et al., *Lab Invest*, 57:112 (1987).
42. T. Sakurai et al., *Nature*, 348:732 (1990).
43. D. Salani et al., *Am J Pathol*, 157:1537 (2000).

44. D. Salani et al., *Am J Pathol*, 157:1703 (2000).
45. P. R. Saxena et al., *Comput Programs Biomed*, 12:63 (1980).
46. J. F. Secombe et al., Vasoactive factors produced by the endothelium. Landes, Austin, pg. 40 (1994).
47. A. C. Sharma et al., *Artif Cells Blood Substit Immobil Biotechnol*, 22:593 (1994).
48. G. Singh et al., *Life Sci*, 54:1901 (1994).
49. P. J. Smith et al. *J Cardiovasc Pharmacol*, 31:S158 (1998).
50. C. W. Song et al., *Int J Radiat Oncol Biol Phys*, 18:903 (1990).
51. C. W. Song et al., *Int J Radiat Oncol Biol Phys*, 17:1041 (1989).
52. Y. Takagi et al., *Biochem Biophys Res Commun*, 168:537 (1990).
53. N. Takuwa et al., *J Biol Chem*, 264:7856 (1989).
54. M. J. van Zwieten, The rat as animal model in breast cancer research. Martinus Nijhoff Publishers, Boston, pg. 206 (1984).
55. P. W. Vaupel, Blood flow, oxygenation, tissue pH distribution, and bioenergetic status of tumors. Ernst Schering, Research Foundation Lecture 23, Berlin (1994).
56. H. Vierhapper et al., *Circulation*, 81:1415 (1990).
57. B. A. Warren, The vascular morphology of tumors. In, *Tumor Blood Circulation*, CRC Press, Boca Raton, pg. 26 (1979).
58. T. Watanabe et al., *J Hypertens*, 19:731 (2001).
59. J. Yamashita et al., *Cancer Res*, 52:4046 (1992).
60. J. Yamashita et al., *Res Commun Chem Pathol Pharmacol*, 74:363 (1991).
61. M. Yanagisawa et al., *Nature*, 332:411 (1988).

Modifications and variations of the invention as hereinbefore set forth can be made without departing from the spirit and scope thereof, and, therefore, only such limitations should be imposed as are indicated by the appended claims.

APPENDIX A
BALANCED $ET_A/ET_B$ ANTAGONISTS

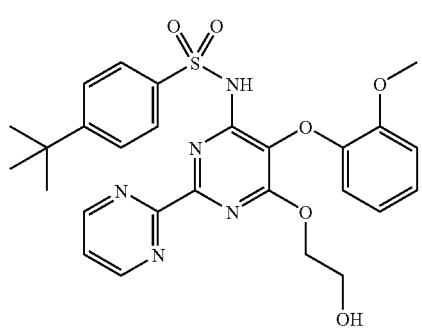

bosentan
1

APPENDIX A
BALANCED $ET_A/ET_B$ ANTAGONISTS

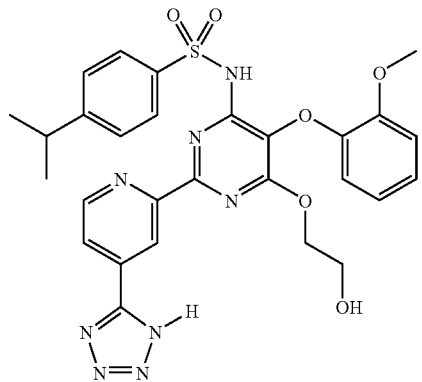

2

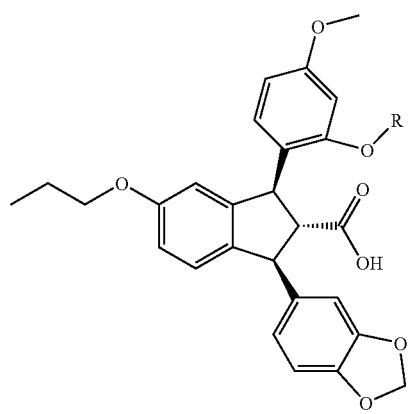

3  R = CH₂CO₂H  SB209670
4  R = CH₂CH₂OH  SB217242

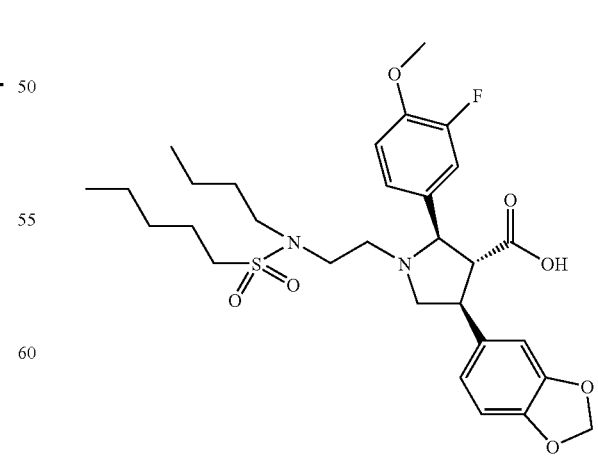

5

23
-continued
APPENDIX A
BALANCED $ET_A/ET_B$ ANTAGONISTS
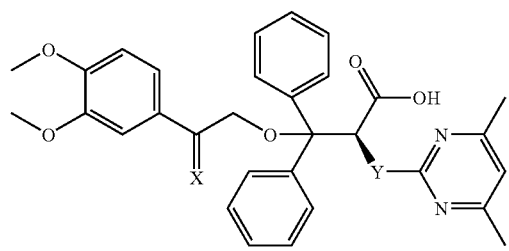
6  X = H$_2$,  Y = CH$_2$   S-LU 302872
7  X = O,    Y = O
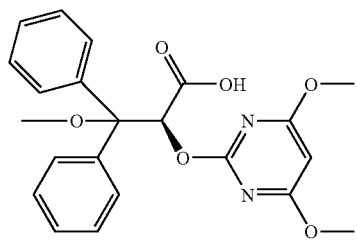
8
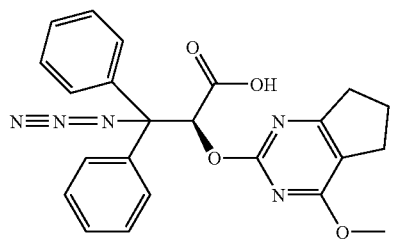
9
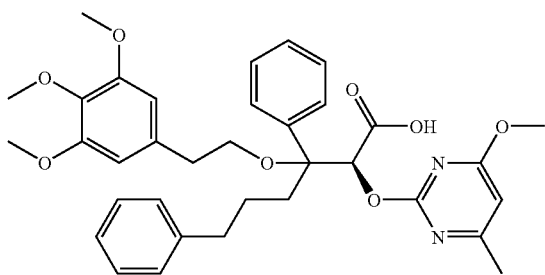
10
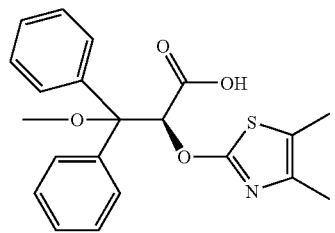
11
24
-continued
APPENDIX A
BALANCED $ET_A/ET_B$ ANTAGONISTS
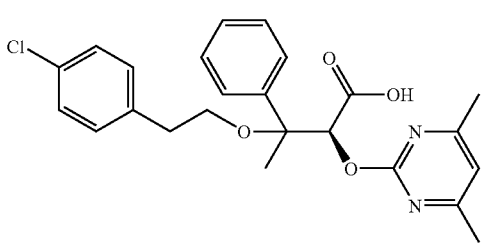
12
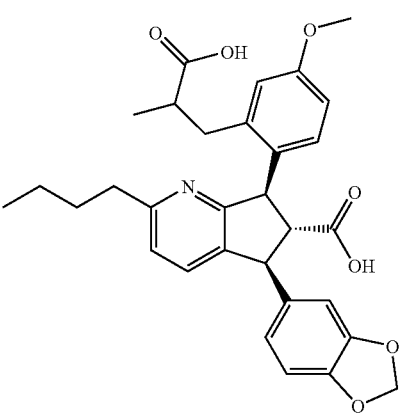
J-104132
13
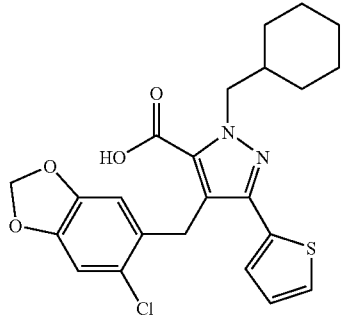
14
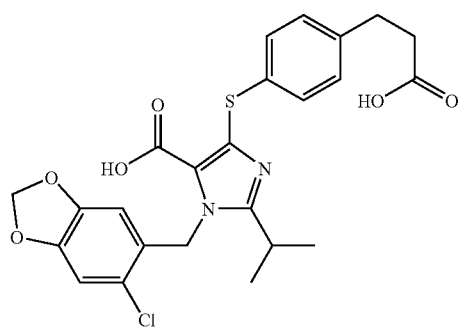
15

APPENDIX A
BALANCED ET$_A$/ET$_B$ ANTAGONISTS
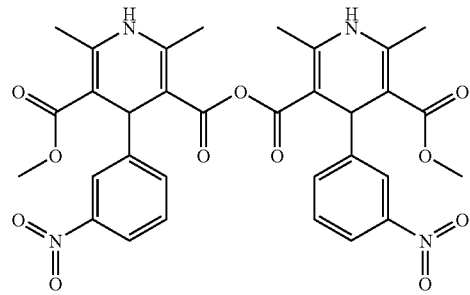
16
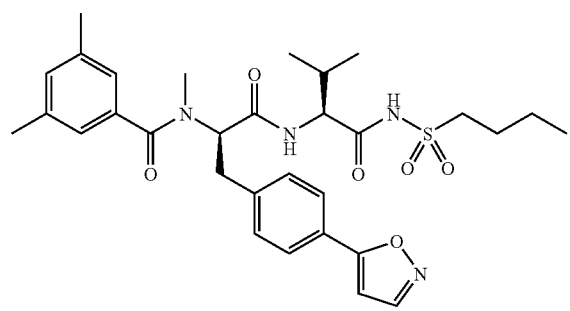
17
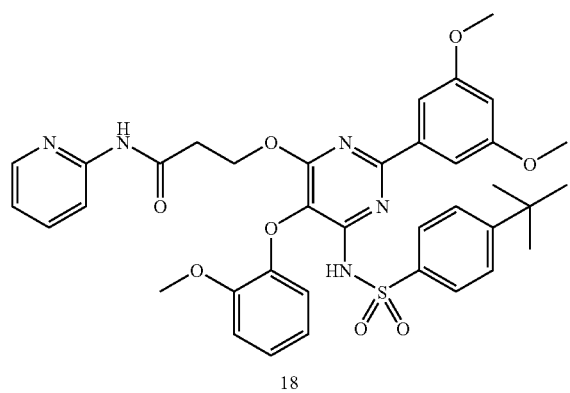
18
APPENDIX A
BALANCED ET$_A$/ET$_B$ ANTAGONISTS
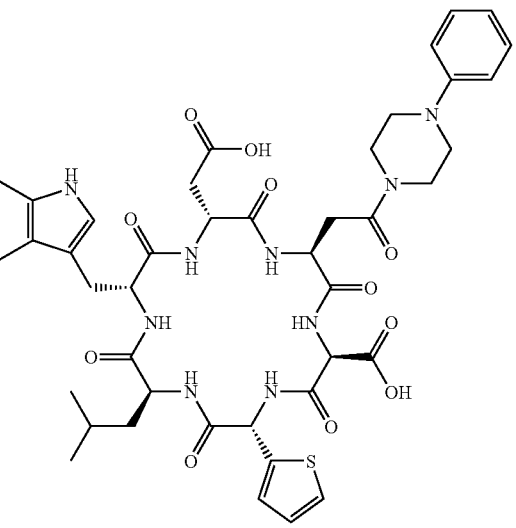
TAK-044
19
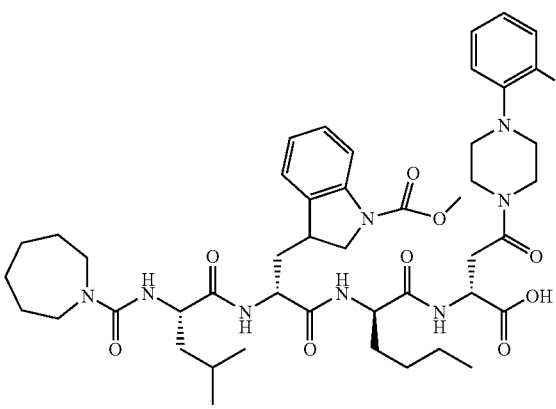
20
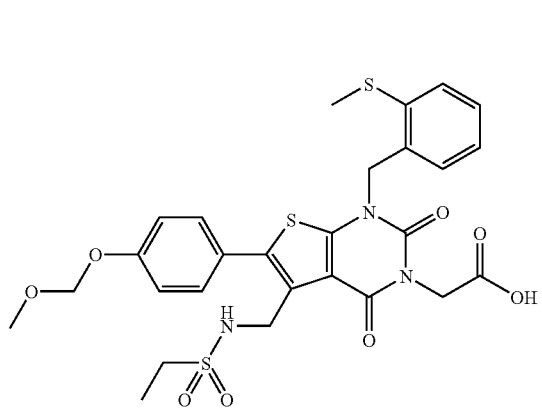
21

APPENDIX A
BALANCED ET$_A$/ET$_B$ ANTAGONISTS
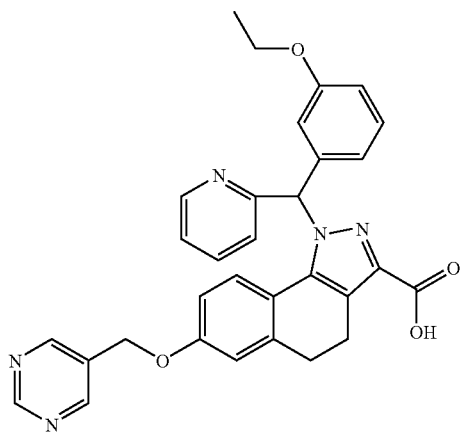
22
APPENDIX B
SELECTIVE ET$_B$ ANTAGONISTS
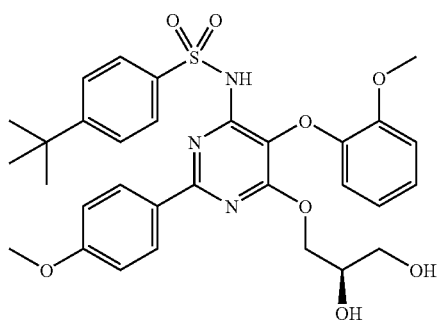
Ro 46-8443
23
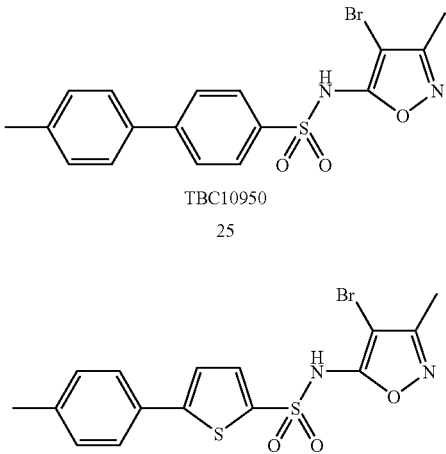
TBC10950
25
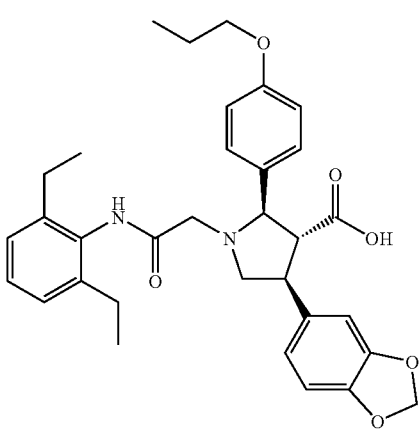
A192621
27
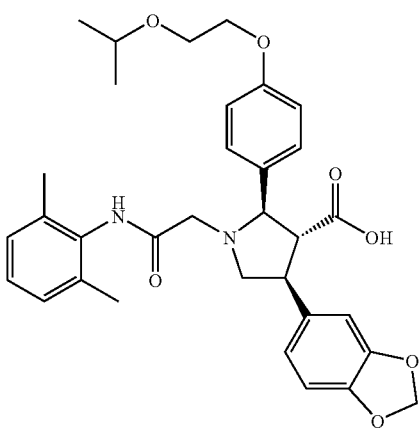
28

APPENDIX B
SELECTIVE ET$_B$ ANTAGONISTS
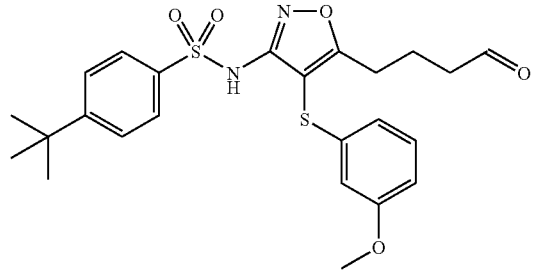
29
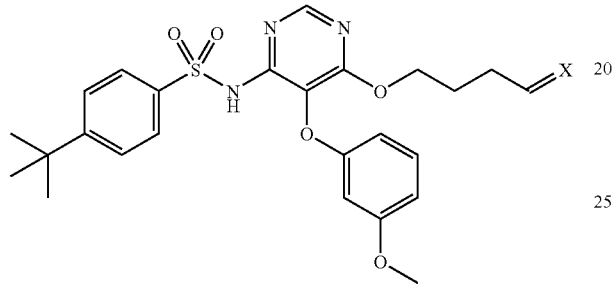
30  X = O
31  X = NNHCO-3-pyridyl
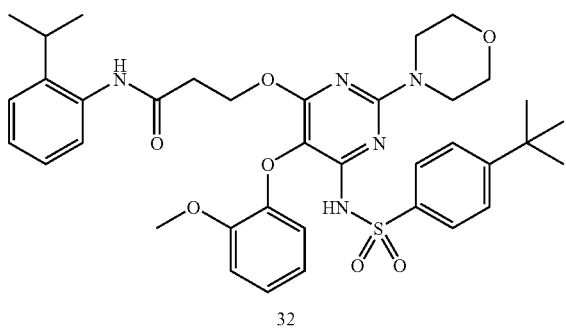
32
APPENDIX C
MISCELLANEOUS ET ANTAGONISTS
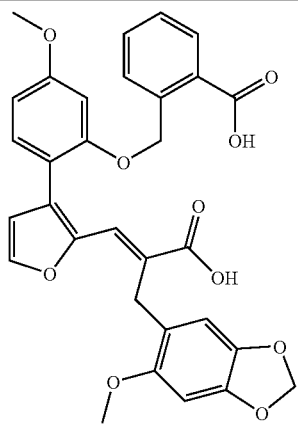
33
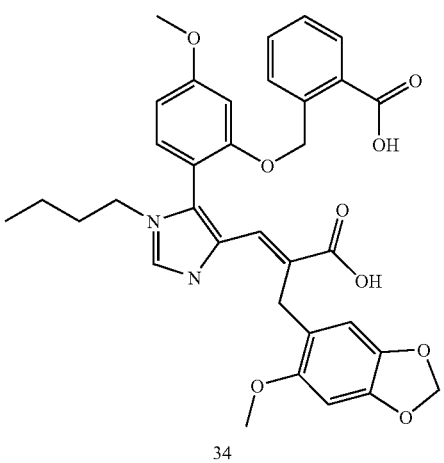
34
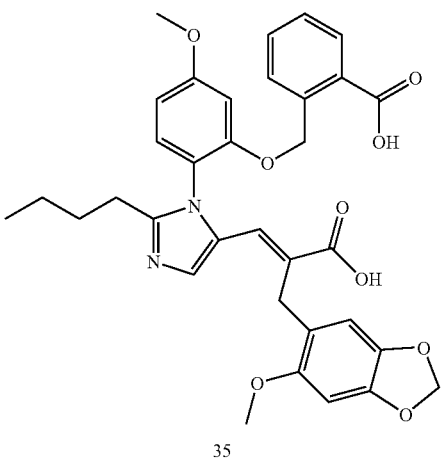
35
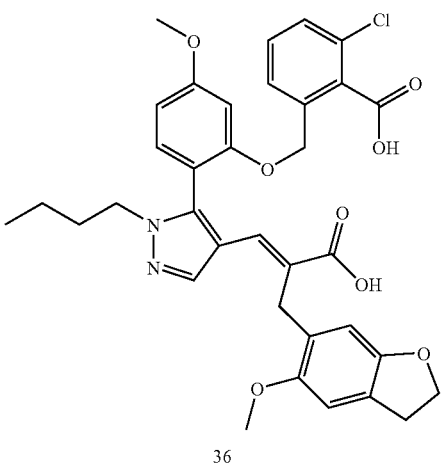
36

APPENDIX C
MISCELLANEOUS ET ANTAGONISTS
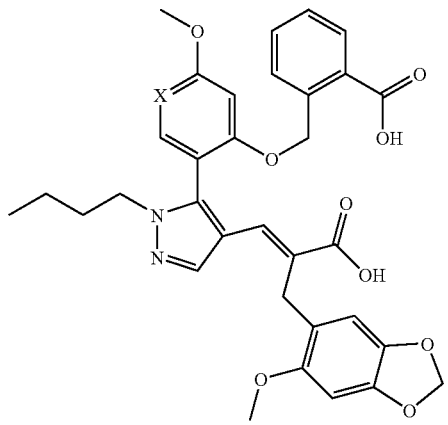
37 X = C
38 X = N
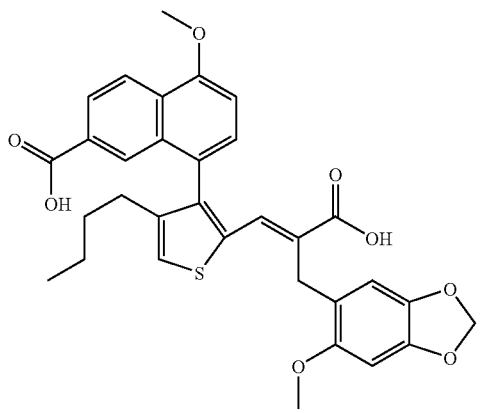
41
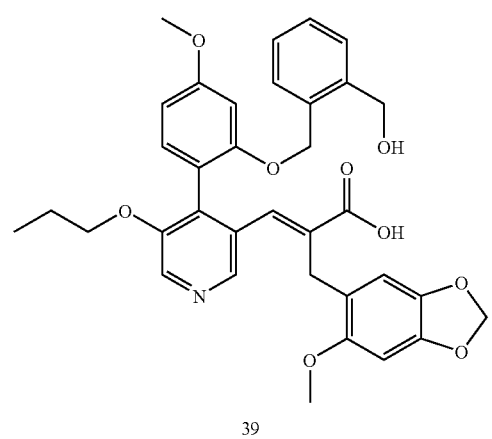
39
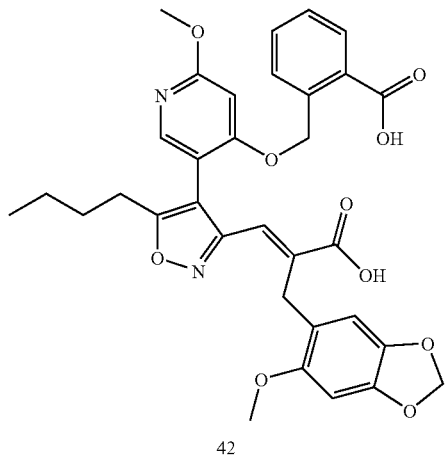
42
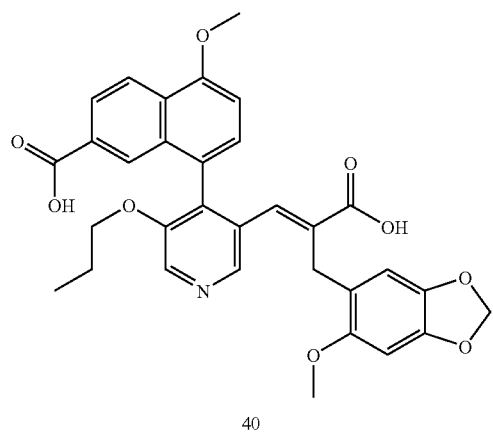
40
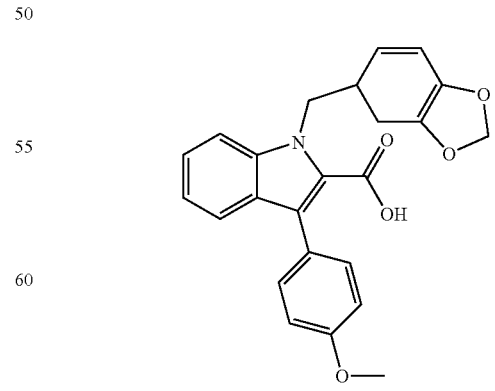
43

APPENDIX C
MISCELLANEOUS ET ANTAGONISTS
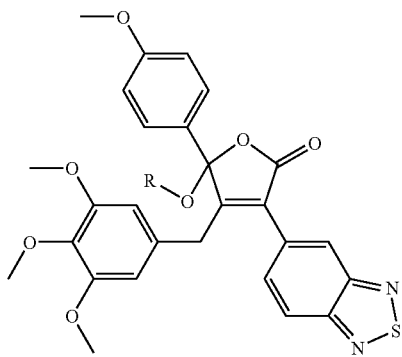
44  R = H
45  R = CONHCH₂CO₂C₂H₅
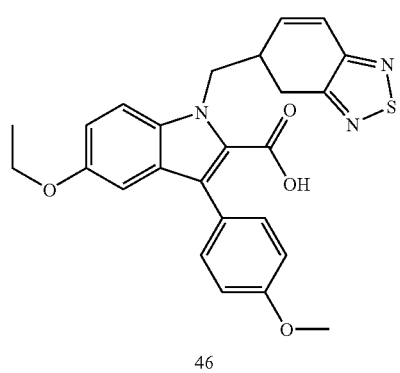
46
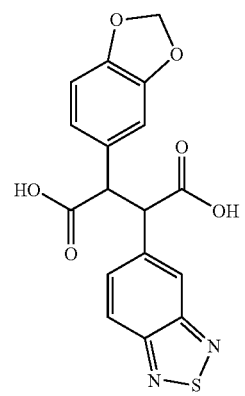
47
APPENDIX C
MISCELLANEOUS ET ANTAGONISTS
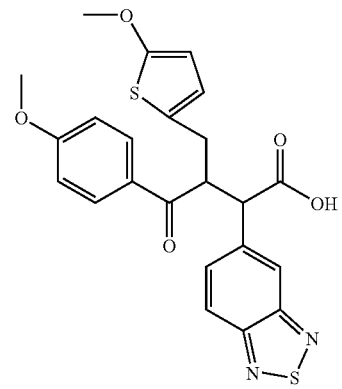
48
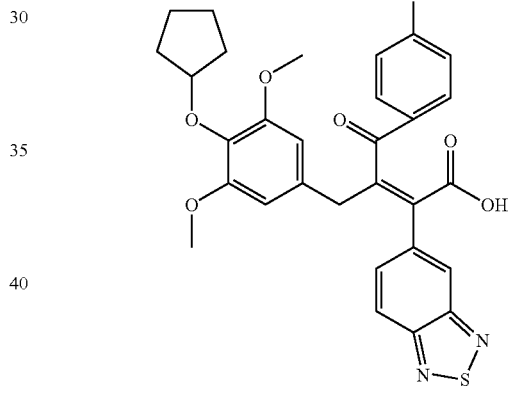
49
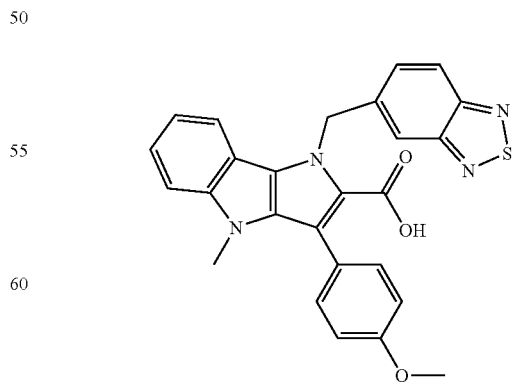
50

APPENDIX C
MISCELLANEOUS ET ANTAGONISTS
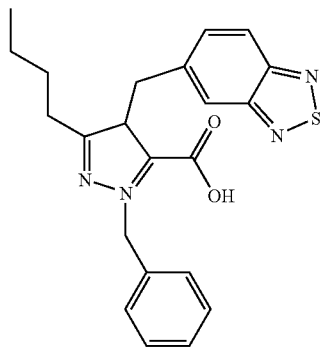
51
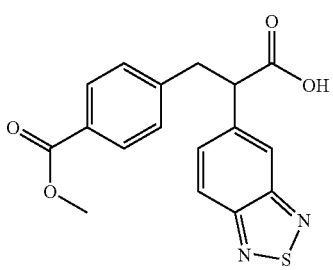
52
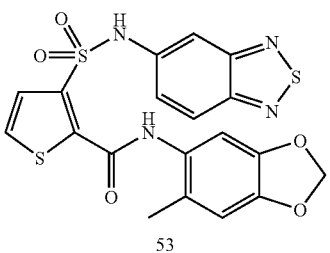
53
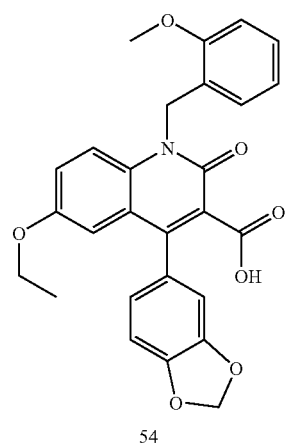
54
APPENDIX C
MISCELLANEOUS ET ANTAGONISTS
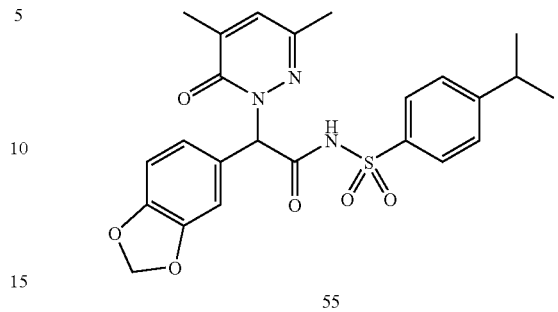
55
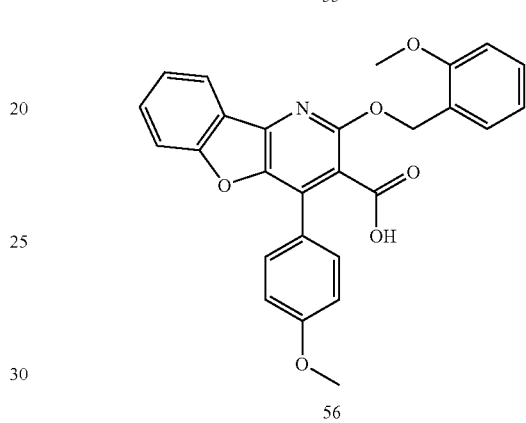
56
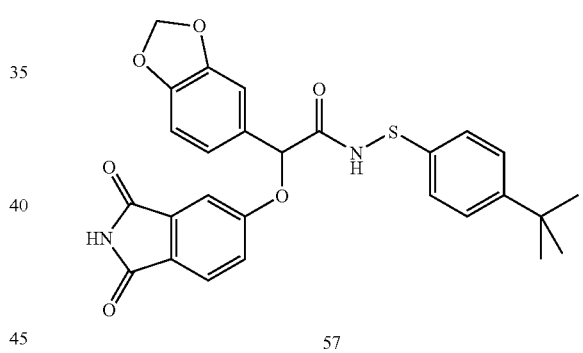
57
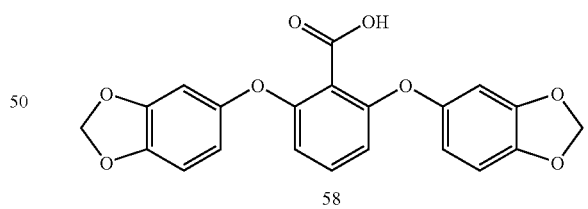
58
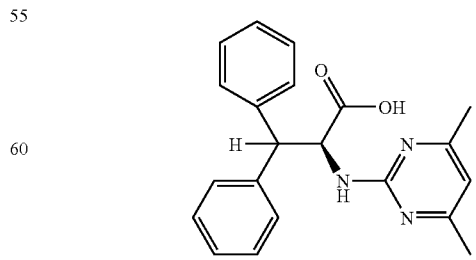
59

APPENDIX C
MISCELLANEOUS ET ANTAGONISTS
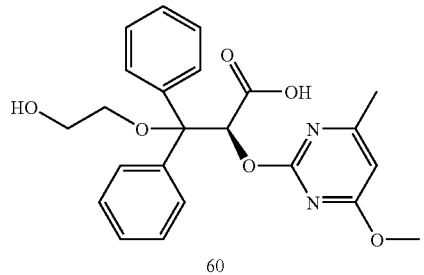
60
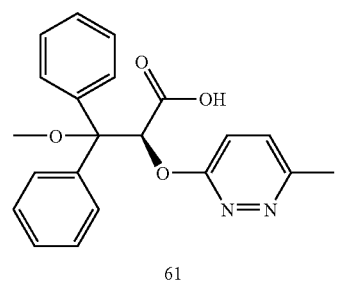
61
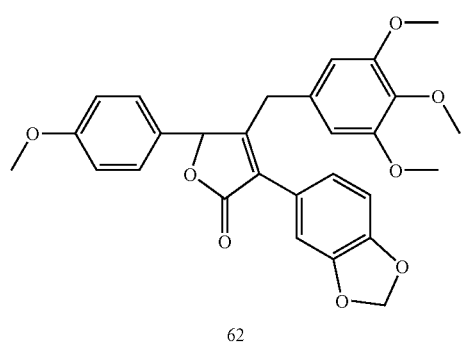
62
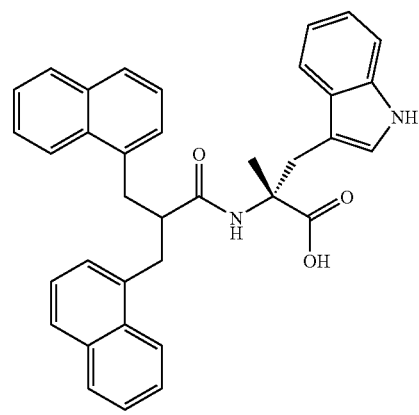
63
APPENDIX C
MISCELLANEOUS ET ANTAGONISTS
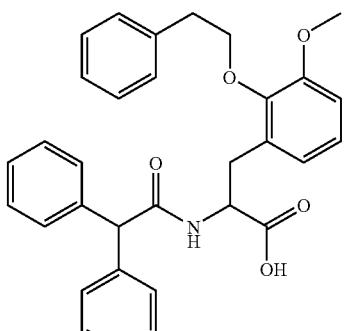
64
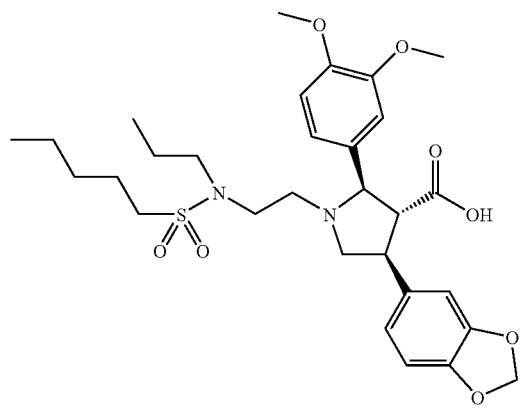
65
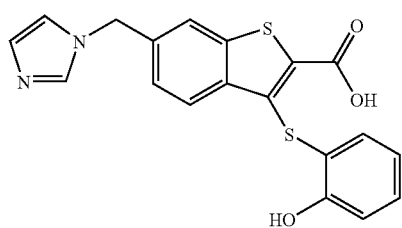
66
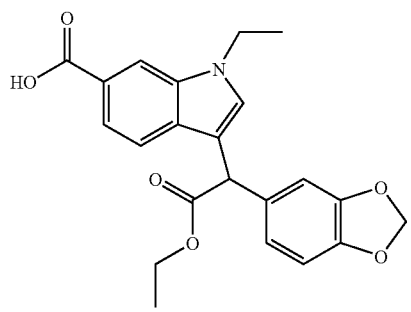
67

APPENDIX C
MISCELLANEOUS ET ANTAGONISTS

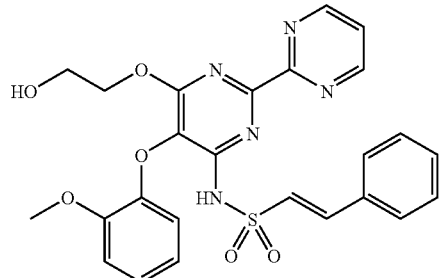

68

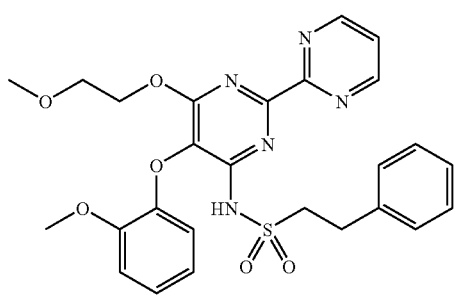

69

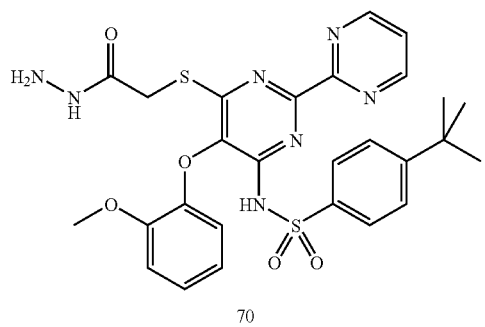

70

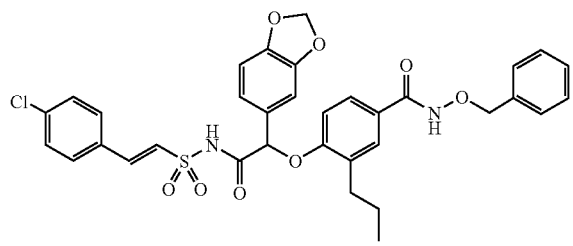

71

APPENDIX C
MISCELLANEOUS ET ANTAGONISTS

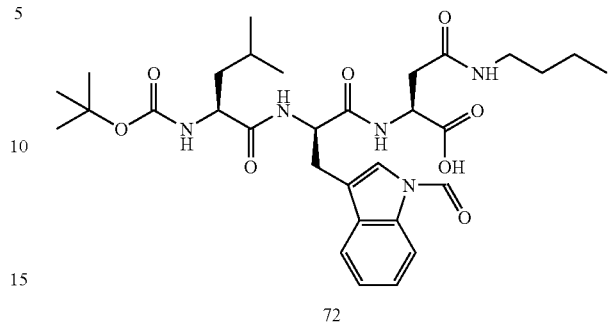

72

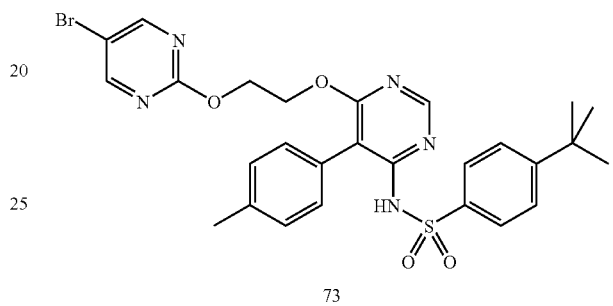

73

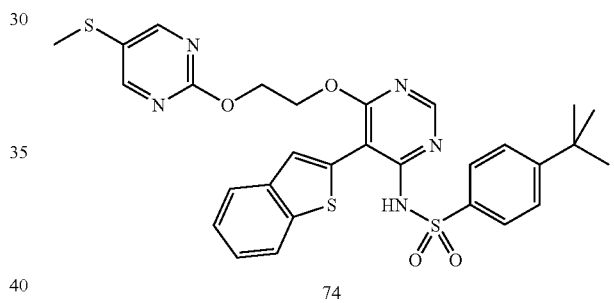

74

What is claimed is:

1. A method of treating a breast tumor comprising administering to a mammal in need thereof a therapeutically effective amount of an endothelin B receptor agonist and a therapeutically effective amount of a chemotherapeutic agent, wherein the endothelin B receptor agonist is IRL 1620.

2. The method of claim 1 wherein the chemotherapeutic agent is selected from the group consisting of adriamycin, camptothecin, carboplatin, cisplatin, daunorubicin, doxorubicin, alpha, beta, or gamma interferon, interleukin 2, irinotecan, docetaxel, paclitaxel, topotecan, and mixtures thereof.

3. The method of claim 1 wherein the endothelin B agonist and the chemotherapeutic agent are administered simultaneously.

4. The method of claim 3 wherein the endothelin B agonist and the chemotherapeutic agent are administered from a single composition.

5. The method of claim 3 wherein the endothelin B agonist and the chemotherapeutic agent are administered from separate compositions.

6. The method of claim 1 wherein the endothelin B agonist and the chemotherapeutic agent are administered sequentially.

7. The method of claim 6 wherein the chemotherapeutic agent is administered prior to the endothelin B agonist.

8. The method of claim 6 wherein the endothelin B agonist is administered prior to the chemotherapeutic agent.

9. The method of claim 1 wherein the mammal is a human.

10. A composition comprising a chemotherapeutic agent, and a second agent that selectively increases blood flow to a solid tumor, wherein said second agent is IRL 1620, and an optional excipient.

11. The composition of claim 10, comprising about 0.1 mg to about 50 mg of the chemotherapeutic agent, about 0.1 mg to about 50 mg of the endothelin B receptor agonist, and an optional excipient, wherein the composition is formulated for oral administration.

12. The composition of claim 10, wherein the composition is formulated for intravenous, buccal, or sublingual administration.

13. An article of manufacture comprising: (a) a packaged composition comprising an IRL 1620; (b) a packaged composition comprising a chemotherapeutic agent; (c) an insert providing instructions for increasing blood flow to a solid tumor by simultaneous or sequential administration of (a) and (b) to treat the solid tumor in a mammal; and (d) a separate container for (a), (b), and (c).

14. An article of manufacture comprising: (a) a packaged composition comprising an IRL 1620 and a chemotherapeutic agent; (b) an insert providing instructions for increasing blood flow to a solid tumor by administration of (a) to treat the solid tumor in a mammal; and (c) a separate container for (a) and (b).

* * * * *